United States Patent
Odaka et al.

(10) Patent No.: US 11,359,220 B2
(45) Date of Patent: *Jun. 14, 2022

(54) SACCHARIFICATION REACTION MIXTURE, SACCHARIFICATION ENZYME COMPOSITION, SUGAR PRODUCTION METHOD, AND ETHANOL PRODUCTION METHOD

(71) Applicant: NISSAN CHEMICAL INDUSTRIES, LTD., Tokyo (JP)

(72) Inventors: Kazutoshi Odaka, Funabashi (JP); Kazutoshi Sekiguchi, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/777,469

(22) PCT Filed: Oct. 12, 2017

(86) PCT No.: PCT/JP2017/037014
§ 371 (c)(1),
(2) Date: May 18, 2018

(87) PCT Pub. No.: WO2018/070478
PCT Pub. Date: Apr. 19, 2018

(65) Prior Publication Data
US 2018/0298412 A1    Oct. 18, 2018

(30) Foreign Application Priority Data

Oct. 14, 2016 (JP) .............................. JP2016-203027

(51) Int. Cl.
| | | |
|---|---|---|
| *C12P 19/14* | (2006.01) | |
| *C13K 1/02* | (2006.01) | |
| *C12P 19/02* | (2006.01) | |
| *C12P 7/10* | (2006.01) | |
| *C12N 9/42* | (2006.01) | |
| *C12N 9/26* | (2006.01) | |

(52) U.S. Cl.
CPC ............ *C12P 19/14* (2013.01); *C12N 9/2411* (2013.01); *C12N 9/2437* (2013.01); *C12P 7/10* (2013.01); *C12P 19/02* (2013.01); *C13K 1/02* (2013.01); *Y02E 50/10* (2013.01)

(58) Field of Classification Search
CPC .. C12P 19/02; C12P 19/14; C12P 7/10; Y02E 50/10; C12N 9/2437; C12N 9/2411; C13K 1/02
See application file for complete search history.

(56) References Cited

U.S. PATENT DOCUMENTS

| | | | |
|---|---|---|---|
| 4,202,939 A | 5/1980 | Mueller et al. | |
| 2011/0250645 A1* | 10/2011 | Schiffino | C12P 7/00 |
| | | | 435/72 |
| 2012/0261269 A1* | 10/2012 | Kagohashi | C01B 33/025 |
| | | | 205/369 |
| 2016/0160252 A1* | 6/2016 | Zhang | C12P 19/02 |
| | | | 435/99 |
| 2017/0218350 A1* | 8/2017 | Sekiguchi | C12P 19/14 |

FOREIGN PATENT DOCUMENTS

| | | |
|---|---|---|
| CN | 101696427 A | 4/2010 |
| CN | 105624207 A | 6/2016 |
| JP | S58-58078 B2 | 12/1983 |
| JP | S63-2595 B2 | 1/1988 |

(Continued)

OTHER PUBLICATIONS

J. Gunner. "Simple Colloid Mixture Examples in Chemistry", https://examples.yourdictionary.com/simple-colloid-mixture-examples-in-chemistry.html, retrieved Feb. 26, 2021 (Year: 2021).*

(Continued)

*Primary Examiner* — Ganapathirama Raghu
(74) *Attorney, Agent, or Firm* — Oliff PLC

(57) ABSTRACT

A saccharification reaction mixture wherein the reaction mixture can saccharify at least one of cellulose and hemicellulose and contains at least one of cellulose and hemicellulose, a saccharification enzyme, silica or a silica-containing substance, and at least one compound (A) selected from the group including a polyhydric alcohol compound represented by the following formula (1) or a derivative thereof and an acetylene glycol represented by formula (2) or an alkylene oxide adduct thereof. The symbols in the chemical formulas are defined in the specification.

[F1]

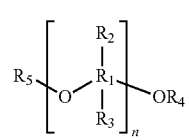

(1)

[F2]

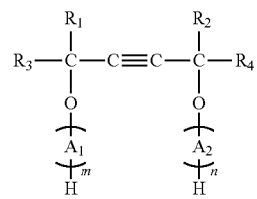

(2)

8 Claims, 4 Drawing Sheets

(56) References Cited

FOREIGN PATENT DOCUMENTS

Figure 1:
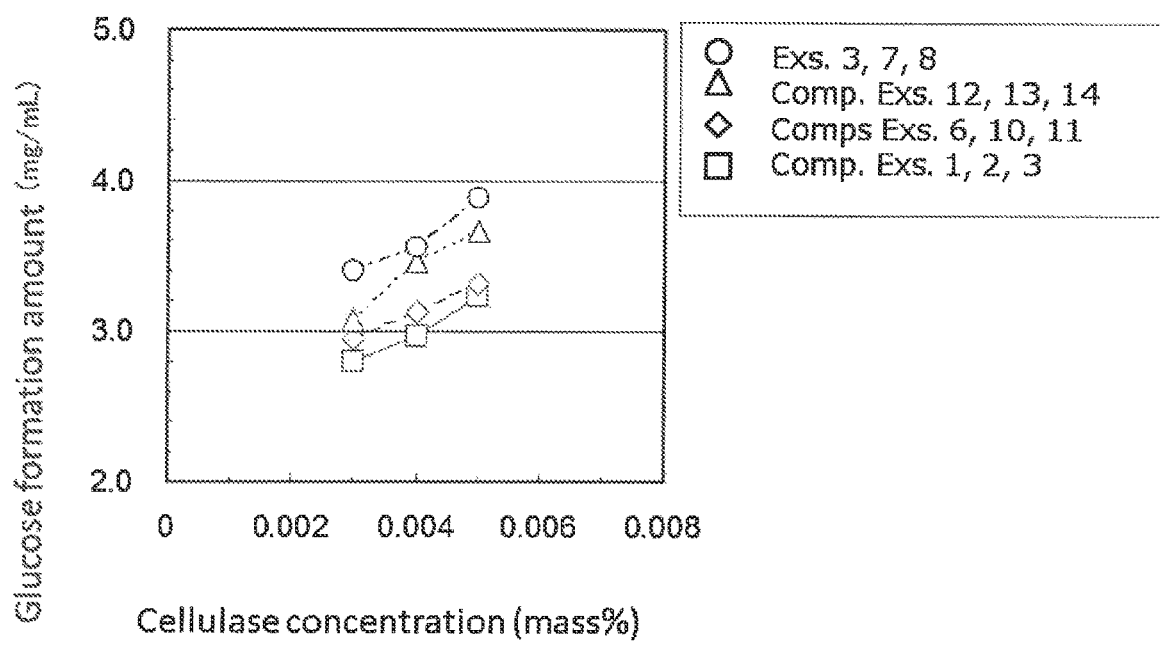

| JP | S63-21475 B2 | 5/1988 |
| JP | H10-66594 A | 3/1998 |
| JP | H11-506934 A | 6/1999 |
| JP | 2006-136263 A | 6/2006 |
| JP | 2006-333749 A | 12/2006 |
| JP | 2009-125006 A | 6/2009 |
| JP | 2009-153448 A | 7/2009 |
| JP | 2012-75379 A | 4/2012 |
| JP | 2013-215187 A | 10/2013 |
| KR | 10-2014-0076140 A | 6/2014 |
| WO | 96/040970 A1 | 12/1996 |
| WO | 2016/021447 A1 | 2/2016 |

OTHER PUBLICATIONS

Ribeiro et al., Kinetics of selective adsorption of impurities from a crude vegetable oil in hexane to activated earths and carbons. Eur Food Res Technol., 2001, vol. 213: 132-138 (Year: 2001).*
Taniguchi et al., Continuous Ethanol Production by Cell-Holding Culture of Yeasts. Eur J Appl Microbiol Biotechnol., 1983, vol. 18: 201-206. (Year: 1983).*
Dec. 26, 2018 Office Action issued in Japanese Patent Application No. 2018-506365.
Jan. 9, 2018 Search Report issued in International Patent Application No. PCT/JP2017/037014.
Mar. 26, 2019 Office Action issued in Taiwanese Patent Application No. 106135022.

* cited by examiner

SACCHARIFICATION REACTION MIXTURE, SACCHARIFICATION ENZYME COMPOSITION, SUGAR PRODUCTION METHOD, AND ETHANOL PRODUCTION METHOD

TECHNICAL FIELD

The present invention relates to a saccharification reaction mixture (or solution or liquid), saccharification enzyme composition, a method for producing a saccharide (or sugar), and a method for producing ethanol.

BACKGROUND ART

Hitherto, there has been known cellulosic bioethanol, which is produced from biomass materials containing cellulose or hemicellulose.

There has also been known a method for producing a saccharide (e.g., glucose) from cellulosic biomass materials containing cellulose or hemicellulose (i.e., a saccharification technique). In the method, the cellulosic biomass materials are hydrolyzed with sulfuric acid. The method involves problems such as corrosion of a reactor and treatment of wastewater. In another known saccharification, cellulosic biomass materials are saccharified in the presence of a solid acid catalyst formed of a support (e.g., carbon or zeoilte) on which sulfo groups are present. This method also has problems of a considerably slow reaction rate due to solid reaction and difficulty in separation of the solid acid catalyst from the unreacted residue. Furthermore, in the above methods, difficulty is encountered in controlling hydrolysis. When the hydrolysis reaction proceeds excessively, the formed saccharide decomposes, to thereby lower the yield of the saccharide of interest.

Also, enzymatic saccharification is known to be performed in the presence of an enzyme (see Patent Document 1). Such a method includes a hydrothermal step of treating a raw material with pressurized hot water, a mechanical crushing step of the hydrothermal treatment product, and a saccharifying step of saccharifying the mechanically crushed product by use of an enzyme. However, according to the method, the enzymatic saccharification rate is low, whereby the produced saccharified liquid does not always have sufficient concentration, which is problematic.

In order to solve the problem, there has been proposed an improved method which can promote enzymatic reaction more efficiently. In the method, the enzyme is immobilized into the meso-porous of a meso-porous silica in the reaction, whereby the enzyme is caused to be present in the reaction system at a higher concentration, as compared with the case in which the enzyme is dissolved in the reaction system (see Patent Document 2). However, this method involves some problems. Specifically, the method requires an additional step of causing the enzyme to be adsorbed into the support for immobilization, and the thus-immobilized enzyme may attain a reduced reaction efficiency of only about 40 to about 50%, as compared with the case of the same enzyme in a non-immobilized state. Furthermore, difficulty is encountered in separating the enzyme-fixed support from the unreacted residue, due to the solid-solid phase reaction.

Also known is a powder-form immobilized enzyme prepared by mixing an enzyme with silica sol, gelling the silica sol to a corresponding silica gel, and crushing the product (see Patent Documents 3 and 4). Even when such a powder-form enzyme is employed, the enzyme can be recovered, but the reaction efficiency is poor. In another known method, dietary fiber containing cellulose is hydrolyzed with a mixture of an enzyme and a silica powder having a particle size of 0.5 μm to 100 μm. However, the effect of mixing the silica powder cannot be definitely proven, and difficulty is encountered in separating the suspended silica powder from the unreacted residue (see Patent Document 5).

Further, there has been proposed a method for saccharifying a cellulosic biomass by use of a saccharifying promoter containing an enzyme and a polyethylene glycol or a derivative thereof (see Patent Document 6). However, the saccharification reaction mixture obtained by use of the saccharifying promoter has an insufficient concentration, which is problematic.

PRIOR ART DOCUMENTS

Patent Documents

Patent Document 1: Japanese Patent Application Laid-Open (kokai) No. 2006-136263
Patent Document 2: Japanese Patent Application Laid-Open (kokai) No. 2009-125006
Patent Document 3: Japanese Patent Publication (kokoku) No. 1988-2595
Patent Document 4: Japanese Patent Publication (kokoku) No. 1988-21475
Patent Document 5: Japanese Patent Application Laid-Open (kokai) No. 1998-66594
Patent Document 6: Japanese Patent Publication (kokoku) No. 1983-58078

SUMMARY OF THE INVENTION

Problems to be Solved by the Invention

Under such circumstances, the present invention has been accomplished. Thus, objects of the present invention are to provide a saccharification reaction mixture (i.e., saccharification reaction liquid, a saccharification enzyme composition, and a method for producing a saccharide (or a sugar) (hereinafter may be referred to as a saccharide production method), which are aimed to enhance saccharification rate by use of an enzyme in a simple step. Another object of the present invention is to provide a method for producing ethanol from a saccharide.

Means for Solving the Problems

Accordingly, a first mode of the present invention, in order to attain the objects, is directed to a saccharification reaction mixture, characterized in that the reaction mixture can saccharify at least one of cellulose and hemicellulose and comprises at least one of cellulose and hemicellulose, a saccharification enzyme, silica or a silica-containing substance, and at least one compound (A) selected from the group consisting of a polyhydric alcohol compound represented by the following formula (1) or a derivative thereof and an acetylene glycol represented by formula (2) or an alkylene oxide adduct thereof.

[F1]

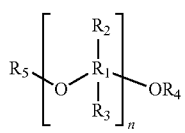

(1)

In formula (1), $R_1$ represents a C1 to C9 linear alkyl group; $R_2$ and $R_3$ each represent a hydrogen atom, a halogen atom, an acyl group, an acetyl group, an amido group, an amino group, an allyl group, an aryl group, an aldehyde group, a C1 to C6 linear or branched alkyl group, a C1 to C6 alkylene group, a C1 to C6 alkenyl group, a C1 to C6 alkoxy group, a carbamoyl group, a carboxyl group, a cyano group, a sulfo group, a sulfonyl group, a tosyl group, a nitro group, a hydroxyl group, a phenyl group, a benzyl group, a phosphoryl group, or a mercapto group, these groups may optionally having a substituent; $R_4$ and $R_5$ each represent a hydrogen atom, an acyl group, an acetyl group, an amido group, an allyl group, an aryl group, an aldehyde group, a C1 to C6 linear or branched alkyl group, a C1 to C6 alkylene group, a C1 to C6 alkenyl group, a carbamoyl group, a carboxyl group, a cyano group, a sulfo group, a sulfonyl group, a tosyl group, a phenyl group, a benzyl group, or a phosphoryl group, these groups may optionally having a substituent; and the number of repeating units (n) is 1 to 500).

[F2]

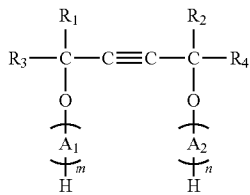

(2)

In formula (2), each of $R_1$, $R_2$, $R_3$, and $R_4$ represents a saturated or unsaturated, linear or branched alkyl or alkenyl group, having a C1 to C10 main chain, the alkyl or alkenyl group having an optional substituent; each of $A_1$ and $A_2$ represents a linear or branched alkylene oxide group having a C2 to C4 main chain (wherein one end (oxygen atom) of the alkylene oxide group is bound to a hydrogen atom, and the other end (carbon atom) is bound to an oxygen atom); and the total number of addition of alkylene oxide units is 0 to 50.

A second mode of the present invention to attain the aforementioned objects is a specific embodiment of the saccharification reaction mixture of the first mode, wherein the silica-containing substance is diatomaceous earth or silica sand.

A third mode of the present invention to attain the aforementioned objects is a specific embodiment of the saccharification reaction mixture of the first or second mode, wherein the ratio by mass of compound (A) to silica contained in the silica or silica-containing substance (compound (A)/silica) is 0.0001 to 1.

A fourth mode of the present invention to attain the aforementioned objects is a specific embodiment of the saccharification reaction mixture of any one of the first to third modes, wherein the polyhydric alcohol compound includes at least one member selected from the group consisting of a monomer, a dimer, a trimer, and an oligomer of a dihydric alcohol, a trihydric alcohol, or a tetrahydric alcohol, and a polyalkylene glycol.

A fifth mode of the present invention to attain the aforementioned objects is a specific embodiment of the saccharification reaction mixture of any one of the first to fourth modes, wherein the polyhydric alcohol compound derivative includes at least one member selected from the group consisting of a polyhydric alcohol ether and a polyalkylene glycol ether.

A sixth mode of the present invention to attain the aforementioned objects is a specific embodiment of the saccharification reaction mixture of any one of the first to fifth modes, wherein the compound (A) includes at least one member selected from the group consisting of ethyelene glycol, propylene glycol, dipropylene glycol, tripropylene glycol, 1,3-butanediol, glycerol, pentaerythritol, polyethyelene glycol, polypropylene glycol, propylene glycol 1-monomethyl ether, 2,4,7,9-tetramethyl-5-decyne-4,7-diol ethylene oxide adduct (ethylene oxide addition (mol); m+n=10), and 2,4,7,9-tetramethyl-5-decyne-4,7-diol (ethylene oxide addition (mol); m+n=30).

A seventh mode of the present invention, in order to attain the objects, is directed to a saccharification enzyme composition, characterized in that the composition can saccharify at least one of cellulose and hemicellulose and comprises a saccharification enzyme, silica or a silica-containing substance, and at least one compound (A) selected from the group consisting of a polyhydric alcohol compound represented by the following formula (1) or a derivative thereof and an acetylene glycol represented by formula (2) or an alkylene oxide adduct thereof, wherein the ratio of the mass of silica contained in the silica or silica-containing substance to the mass of compound (A) (compound (A)/silica) is 0.0001 to 1.

[F3]

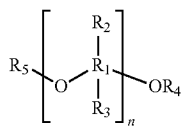

(1)

In formula (1), $R_1$ represents a C1 to C9 linear alkyl group; $R_2$ and $R_3$ each represent a hydrogen atom, a halogen atom, an acyl group, an acetyl group, an amido group, an amino group, an allyl group, an aryl group, an aldehyde group, a C1 to C6 linear or branched alkyl group, a C1 to C6 alkylene group, a C1 to C6 alkenyl group, a C1 to C6 alkoxy group, a carbamoyl group, a carboxyl group, a cyano group, a sulfo group, a sulfonyl group, a tosyl group, a nitro group, a hydroxyl group, a phenyl group, a benzyl group, a phosphoryl group, or a mercapto group, these groups may optionally having a substituent; $R_4$ and $R_5$ each represent a hydrogen atom, an acyl group, an acetyl group, an amido group, an allyl group, an aryl group, an aldehyde group, a C1 to C6 linear or branched alkyl group, a C1 to C6 alkylene group, a C1 to C6 alkenyl group, a carbamoyl group, a carboxyl group, a cyano group, a sulfo group, a sulfonyl group, a tosyl group, a phenyl group, a benzyl group, or a phosphoryl group, these groups may optionally having a substituent; and the number of repeating units (n) is 1 to 500).

[F4]

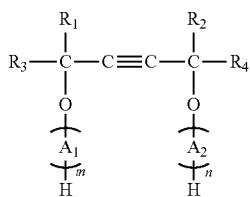

(2)

In formula (2), each of $R_1$, $R_2$, $R_3$, and $R_4$ represents a saturated or unsaturated, linear or branched alkyl or alkenyl group, having a C1 to C10 main chain, the alkyl or alkenyl group having an optional substituent; each of $A_1$ and $A_2$ represents a linear or branched alkylene oxide group having a C2 to C4 main chain (wherein one end (oxygen atom) of the alkylene oxide group is bound to a hydrogen atom, and the other end (carbon atom) is bound to an oxygen atom); and the total number of addition of alkylene oxide units is 0 to 50.

An eighth mode of the present invention to attain the aforementioned objects is a specific embodiment of the saccharification enzyme composition of the seventh mode, wherein the silica-containing substance is diatomaceous earth or silica sand.

A ninth mode of the present invention to attain the aforementioned objects is a specific embodiment of the saccharification enzyme composition of the seventh or eighth mode, wherein the polyhydric alcohol compound includes at least one member selected from the group consisting of a monomer, a dimer, a trimer, and an oligomer of a dihydric alcohol, a trihydric alcohol, or a tetrahydric alcohol, and a polyalkylene glycol.

A tenth mode of the present invention to attain the aforementioned objects is a specific embodiment of the saccharification enzyme composition of any one of the seventh to ninth modes, wherein the polyhydric alcohol compound derivative includes at least one member selected from the group consisting of a polyhydric alcohol ether and a polyalkylene glycol ether.

An eleventh mode of the present invention to attain the aforementioned objects is a specific embodiment of the saccharification enzyme composition of any one of the seventh to tenth modes, wherein the compound (A) includes at least one member selected from the group consisting of ethyelene glycol, propylene glycol, dipropylene glycol, tripropylene glycol, 1,3-butanediol, glycerol, pentaerythritol, polyethyelene glycol, polypropylene glycol, propylene glycol 1-monomethyl ether, 2,4,7,9-tetramethyl-5-decyne-4,7-diol ethylene oxide adduct (ethylene oxide addition (mol); m+n=10), and 2,4,7,9-tetramethyl-5-decyne-4,7-diol (ethylene oxide addition (mol); m+n=30).

A twelfth mode of the present invention, in order to attain the objects, is directed to a method for producing a saccharide by use of a saccharification reaction mixture which can saccharify at least one of cellulose and hemicellulose, wherein the method comprise employing a saccharification reaction mixture comprising at least one of cellulose and hemicellulose, a saccharification enzyme, silica or a silica-containing substance, and at least one compound (A) selected from the group consisting of a polyhydric alcohol compound represented by the following formula (1) or a derivative thereof and an acetylene glycol represented by formula (2) or an alkylene oxide adduct thereof.

[F5]

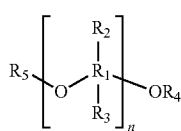

(1)

In formula (1), $R_1$ represents a C1 to C9 linear alkyl group; $R_2$ and $R_3$ each represent a hydrogen atom, a halogen atom, an acyl group, an acetyl group, an amido group, an amino group, an allyl group, an aryl group, an aldehyde group, a C1 to C6 linear or branched alkyl group, a C1 to C6 alkylene group, a C1 to C6 alkenyl group, a C1 to C6 alkoxy group, a carbamoyl group, a carboxyl group, a cyano group, a sulfo group, a sulfonyl group, a tosyl group, a nitro group, a hydroxyl group, a phenyl group, a benzyl group, a phosphoryl group, or a mercapto group, these groups may optionally having a substituent; $R_4$ and $R_5$ each represent a hydrogen atom, an acyl group, an acetyl group, an amido group, an allyl group, an aryl group, an aldehyde group, a C1 to C6 linear or branched alkyl group, a C1 to C6 alkylene group, a C1 to C6 alkenyl group, a carbamoyl group, a carboxyl group, a cyano group, a sulfo group, a sulfonyl group, a tosyl group, a phenyl group, a benzyl group, or a phosphoryl group, these groups may optionally having a substituent; and the number of repeating units (n) is 1 to 500).

[F6]

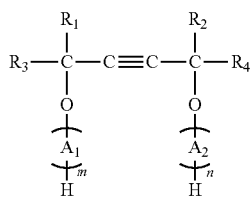

(2)

In formula (2), each of $R_1$, $R_2$, $R_3$, and $R_4$ represents a saturated or unsaturated, linear or branched alkyl or alkenyl group, having a C1 to C10 main chain, the alkyl or alkenyl group having an optional substituent; each of $A_1$ and $A_2$ represents a linear or branched alkylene oxide group having a C2 to C4 main chain (wherein one end (oxygen atom) of the alkylene oxide group is bound to a hydrogen atom, and the other end (carbon atom) is bound to an oxygen atom); and the total number of addition of alkylene oxide units is 0 to 50.

A thirteenth mode of the present invention to attain the aforementioned objects is a specific embodiment of the saccharide production method of the twelfth mode, wherein the silica-containing substance is diatomaceous earth or silica sand.

A fourteenth mode of the present invention to attain the aforementioned objects is a specific embodiment of the saccharide production method of the twelfth or thirteenth mode, wherein the ratio of the mass of silica contained in the silica or silica-containing substance to the mass of compound (A) (compound (A)/silica) is 0.0001 to 1.

A fifteenth mode of the present invention to attain the aforementioned objects is a specific embodiment of the saccharide production method of any one of the twelfth to fourteenth modes, wherein the polyhydric alcohol compound includes at least one member selected from the group consisting of a monomer, a dimer, a trimer, and an oligomer of a dihydric alcohol, a trihydric alcohol, or a tetrahydric alcohol, and a polyalkylene glycol.

A sixteenth mode of the present invention to attain the aforementioned objects is a specific embodiment of the saccharide production method of any one of the twelfth to fifteenth modes, wherein the polyhydric alcohol compound derivative includes at least one member selected from the group consisting of a polyhydric alcohol ether and a polyalkylene glycol ether.

A seventeenth mode of the present invention to attain the aforementioned objects is a specific embodiment of the saccharide production method of any one of the twelfth to sixteenth modes, wherein the compound (A) includes at least one member selected from the group consisting of ethyelene glycol, propylene glycol, dipropylene glycol, tripropylene glycol, 1,3-butanediol, glycerol, pentaerythritol, polyethyelene glycol, polypropylene glycol, propylene glycol 1-monomethyl ether, 2,4,7,9-tetramethyl-5-decyne-4,7-diol ethylene oxide adduct (ethylene oxide addition (mol); m+n=10), and 2,4,7,9-tetramethyl-5-decyne-4,7-diol (ethylene oxide addition (mol); m+n=30).

An eighteenth mode of the present invention, in order to attain the objects, is directed to a method for producing ethanol, characterized in that the method comprises subjecting a saccharide produced through a production method of any one of the twelfth to seventeenth modes to ethanol fermentation in the presence of a microorganism which can cause fermentation (hereinafter referred to as "fermentation microorganism"), to thereby produce ethanol.

A nineteenth mode of the present invention to attain the aforementioned objects is a specific embodiment of the ethanol production method of the eighteenth mode, wherein the fermentation microorganism is added to the saccharide production method, to thereby simultaneously carry out sugar production and ethanol fermentation.

A twentieth mode of the present invention to attain the aforementioned objects is a specific embodiment of the ethanol production method of the eighteenth or nineteenth mode, wherein the fermentation microorganism is a yeast, a mold, or a bacterium.

A twenty-first mode of the present invention to attain the aforementioned objects is a specific embodiment of the ethanol production method of the twentieth mode, wherein the fermentation microorganism is a microorganism belonging to the *Saccharomyces*, a microorganism belonging to the *Zymomonas*, a microorganism belonging to the *Pichia*, a microorganism belonging to the *Candida*, a microorganism belonging to the *Zymobacter*, a microorganism belonging to the *Corynebacterium*, a microorganism belonging to the *Kluyveromyces*, or a microorganism belonging to the *Escherichia*.

A twenty-second mode of the present invention to attain the aforementioned objects is a specific embodiment of the ethanol production method of any one of the eighteenth to twenty-first modes, wherein ethanol fermentation is carried out at 15° C. to 35° C.

Effects of the Invention

The present invention enables provision of a saccharification reaction mixture, a saccharification enzyme composition, and a saccharide production method, which are aimed to enhance saccharification reaction efficiency by use of an enzyme in a simple step, as well as an ethanol production method employing the produced saccharide.

BRIEF DESCRIPTION OF THE INVENTION

FIG. 1 A graph showing enhancement in saccharification reaction efficiency through addition of tripropylene glycol (Examples 3, 7, and 8, and Comparative Examples 1 to 3, 6, and 10 to 14).

Figure 2:
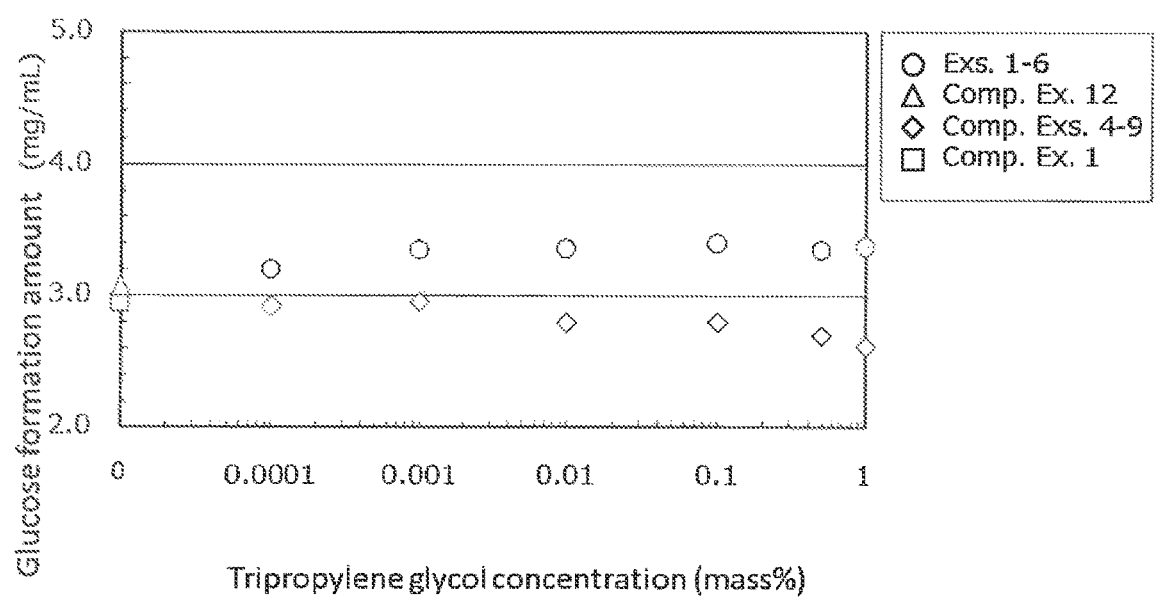

FIG. 2 A graph showing enhancement in saccharification reaction efficiency vs. tripropylene glycol concentration (Examples 1 to 6, and Comparative Examples 1, 4 to 9, and 12).

Figure 3:
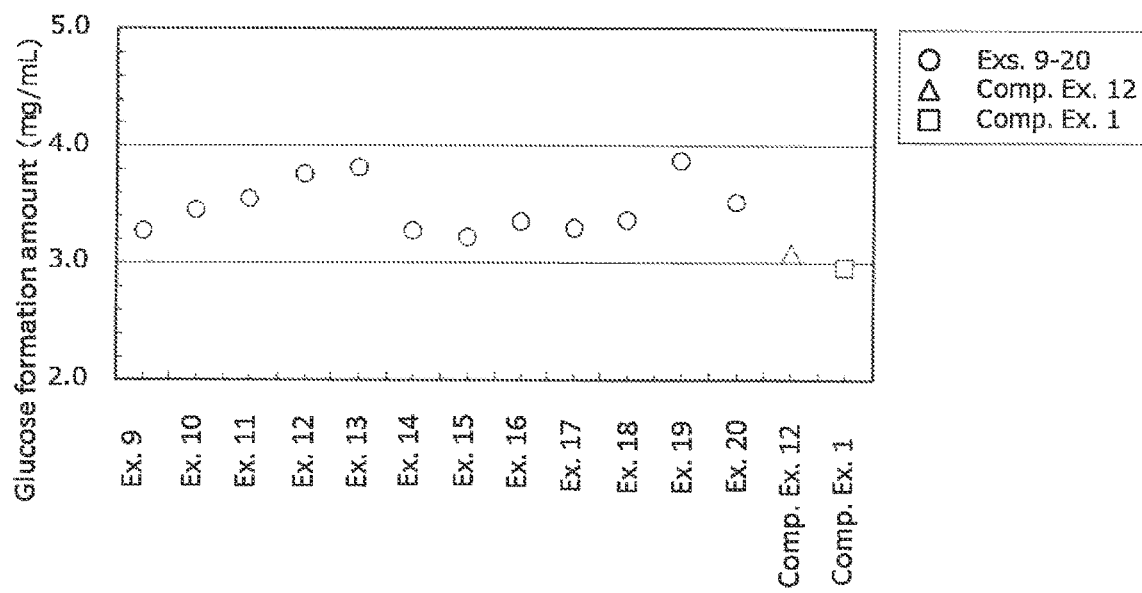

FIG. 3 A graph showing enhancement in saccharification reaction efficiency through addition of a polyhydric alcohol compound, a polyhydric alcohol compound derivative, or an acetylene glycol alkylene oxide adduct (Examples 9 to 20, and Comparative Examples 1 and 12).

Figure 4:
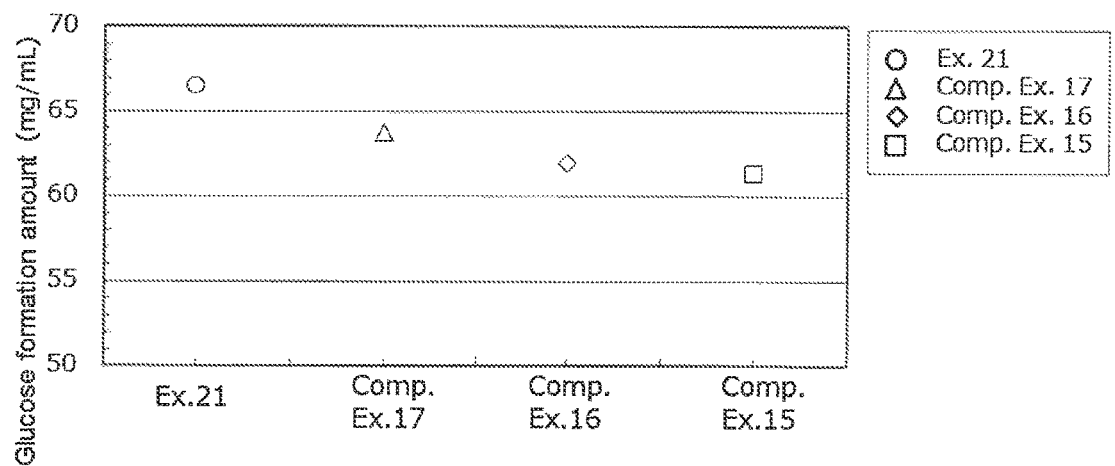

FIG. 4 A graph showing enhancement in saccharification reaction efficiency through addition of PPG 1000 (Example 21 and Comparative Examples 15 to 17).

Figure 5:
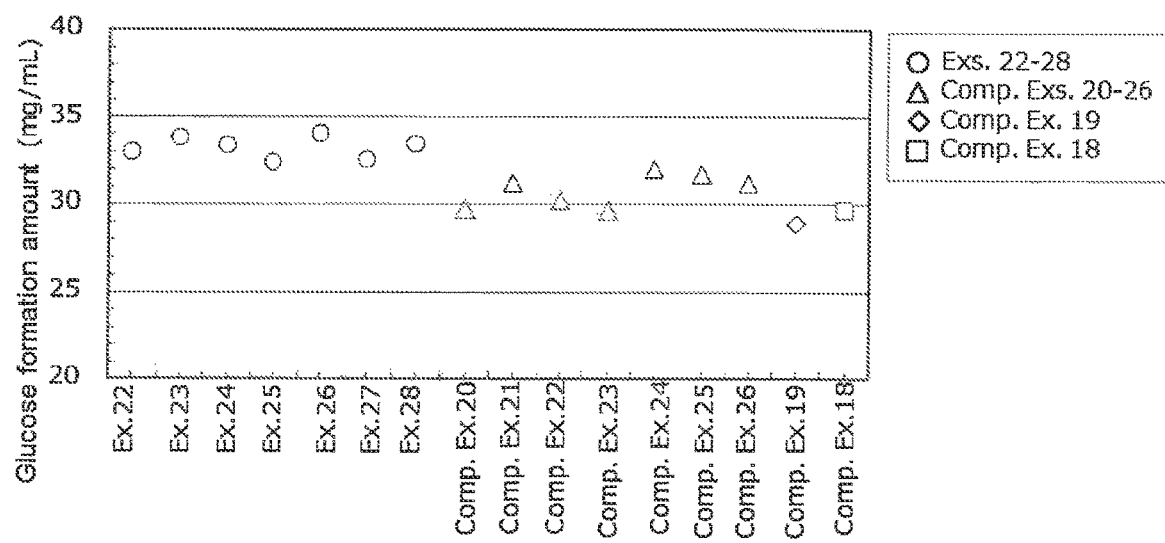

FIG. 5 A graph showing enhancement in saccharification reaction efficiency through addition of PPG 1000 (Examples 22 to 28, and Comparative Examples 18 to 26).

Figure 6:
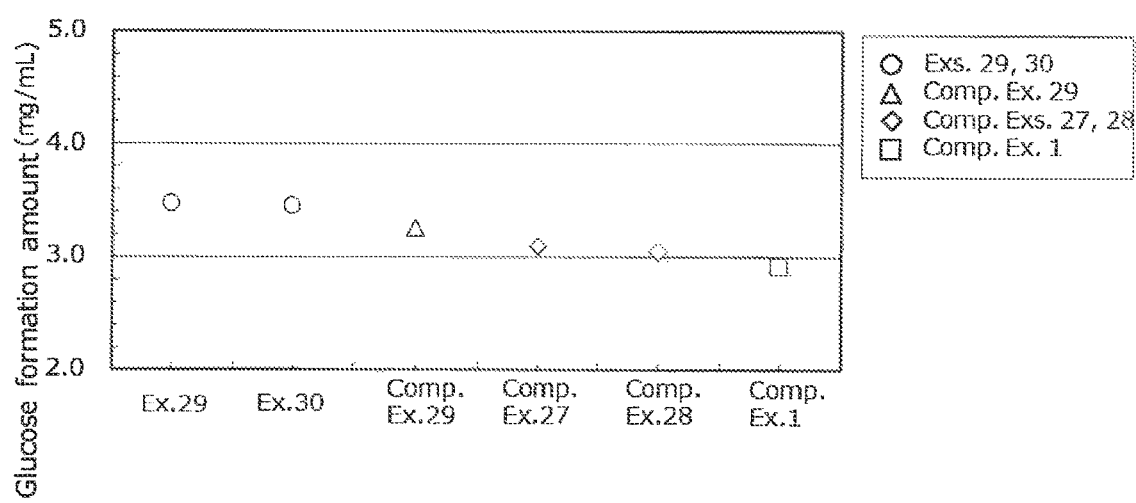

FIG. 6 A graph showing enhancement in saccharification reaction efficiency through addition of PPG 1000 or 2,4,7,9-tetramethyl-5-decyne-4,7-diol ethylene oxide adduct (Examples and 29 and 30, and Comparative Examples 1, and 27 to 29).

Figure 7:
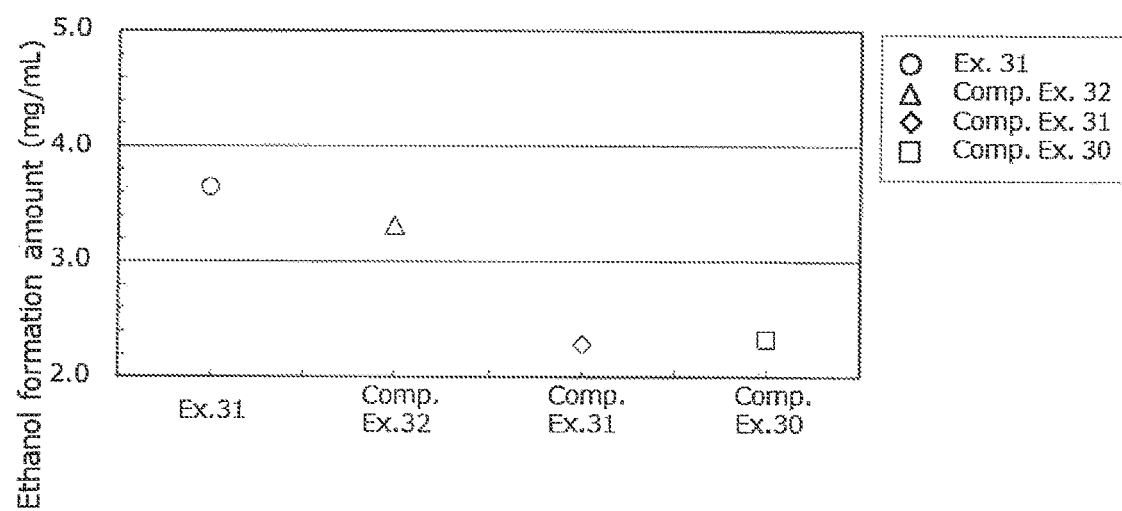

FIG. 7 A graph showing enhancement in ethanol fermentation efficiency through addition of PPG 1000 (Example 31 and Comparative Examples 30 to 32).

MODES FOR CARRYING OUT THE INVENTION

In the present invention, at least one of cellulose and hemicellulose is used as a raw material for producing a saccharide such as glucose.

Generally, the cellulose or hemicellulose is contained in cellulosic biomass materials such as agricultural, forest, and fishery products (e.g., broad-leaved trees and coniferous trees) and wastes thereof. Specific examples include bagasse, rice straw, corn stover, oil palm empty fruit bunches, wood fiber, wood chips, veneer waste chips, sawdust, pulp, waste paper, cotton, sea squirt, and acetic acid bacteria. No particular limitation is imposed on the biomass material, so long as it is derived from cellulosic biomass materials. Such biomass materials may be used singly or in combination of two or more species.

Among them, cellulose and hemicellulose derived from sawdust of eucalyptus wood (broad-leaved tree), sawdust of Japanese cedar (coniferous tree), bagasse, rice straw, corn stover, oil palm empty fruit bunches, and cotton are preferred. Although no precise mechanism has been elucidated, these preferred materials are easy to fibrillate, leading to high-yield sugar production.

As used herein, "cellulose" refers to a polymer formed through polymerization of glucose molecules via β-1,4-glucoside bonds, and "hemicellulose" refers to a water-insoluble polysaccharide other than cellulose, which polysaccharide is a polymer formed through polymerization of glucose molecules of glucose, xylose, mannose, galactose, etc. via glucoside bonds.

The cellulose may include cellooligosaccharide or cellobiose, which is a partial decomposition product of cellulose, and may be crystalline or non-crystalline. Also, the cellulose may be a carboxymethylated, aldehydified, or esterified derivative. Notably, as mentioned above, no particular limitation is imposed on the species of cellulose and hemicellulose, so long as they are derived from a biomass material. Thus, the cellulose or hemicellulose may be derived from plants, fungi, or bacteria.

In the present invention, an enzyme predominantly contains cellulase is used as the saccharification enzyme. The cellulase refers to an enzyme which decomposes cellulose or hemicellulose to a saccharide such as glucose.

No particular limitation is imposed on the microorganism which provides such a saccharification enzyme. Examples of the microorganism include bacteria belonging to the *Acremonium*, to the *Aspergillus*, to the *Chaetomium*, to the *Fusarium*, to the *Humicola*, to the *Irpex*, to the *Phanerochaete*, to the *Penicillium*, to the *Schizophyllum*, to the *Sporotrichum*, to the *Trametes*, and to the *Trichoderma*. Examples of the microorganism also include bacteria belonging to the *Clostridium*, to the *Pseudomonas*, to the *Cellulomonas*, to the *Ruminococcus*, and to the *Bacillus*, and actinomycetes belonging to the *Sulfolobus*, to the *Streptomyces*, to the *Thermoactinomyces*, and to the *Thermomonospora*. These saccharification enzymes may be artificially modified and may be used singly or in combination of two or more species.

Among them, enzymes derived from bacteria belonging to the *Aspergillus* and to the *Trichoderma* are preferred, since they have high enzymatic activity on crystalline cellulose.

Alternatively, the cellulase may be a group of enzymes. The enzyme group includes endoglucanase (EC 3.2.1.74), cellobiohydrase (EC 3.2.1.91), β-glucosidase (EC 23.2.4.1, EC 3.2.1.21), etc. Notably, in the present invention, cellulases derived from different bacterial species are preferably used in combination. In this case, saccharization of cellulose or hemicellulose can be more promoted by virtue of the synergistic effect.

The aforementioned cellulase generally has an optimum enzymatic activity at a pH of 3 to 6. However, the cellulase may be an alkaline cellulase, having an optimum enzymatic activity at a pH of 6 to 10. Also, the aforementioned cellulase generally has an optimum enzymatic activity at a reaction temperature of 25° C. to 50° C. However, the cellulase may be a heat-resistant cellulase, having an optimum enzymatic activity at a reaction temperature of 70° C. to 100° C.

In the present invention, silica, diatomaceous earth, or silica sand may be used as the silica or silica-containing substance. The aforementioned diatomaceous earth and silica sand serving as a silica-containing substance are natural products mainly containing silica. Silica collectively refers to compounds containing at least silicon dioxide. Generally, surfaces of silica particles have silanol groups. The silica particles may have a spherical or non-spherical shape. The particles may have a dense (non-hollow) structure or a porous structure, and may be amorphous or crystalline in terms of crystallinity. In use, the particles may be in a form of powder, suspension, or dispersion. The surfaces of silica particles may be partially modified with a functional group other than a silanol group. Alternatively, a compound other than silica may be reacted with a silicon-containing species such as a silane coupling agent, a silicon alkoxide, or silicate ions, to thereby form a silica surface layer. Among these materials, colloidal silica, diatomaceous earth, and silica sand are preferably employed.

In the present invention, the colloidal silica has a mean primary particle size of 1 nm to 400 nm, preferably 5 nm to 350 nm, and is dispersed in the saccharification reaction mixture. The mean primary particle size is calculated by the formula: D (nm)=2720/S, wherein S represents a specific surface area (m$^2$/g) as determined through the nitrogen adsorption method (BET method). In use, the colloidal silica is dispersed in a dispersion solvent such as water, methanol, ethanol, acetone, methyl ethyl ketone, or ethylene glycol, to form a dispersion liquid. The dispersion liquid is generally called colloidal liquid, sol, or the like. In the present invention, so long as the enzymatic activity is not inhibited, any dispersion solvent may be used. Preferably, the dispersion solvent is water, ethanol, or the like.

The colloidal silica may be produced through a water glass method employing water glass as a raw material, an alkoxide method employing a metal alkoxide as a raw material, or a vapor phase method employing a silicon chloride compound as a raw material. Colloidal silica produced through any of these methods may be employed, but colloidal silica produced through the water glass method is preferably employed.

In the present invention, in formula (1), $R_1$ represents a C1 to C9 linear alkyl group; $R_2$ and $R_3$ each represent a hydrogen atom, a halogen atom, an acyl group, an acetyl group, an amido group, an amino group, an allyl group, an aryl group, an aldehyde group, a C1 to C6 linear or branched alkyl group, a C1 to C6 alkylene group, a C1 to C6 alkenyl group, a C1 to C6 alkoxy group, a carbamoyl group, a carboxyl group, a cyano group, a sulfo group, a sulfonyl group, a tosyl group, a nitro group, a hydroxyl group, a phenyl group, a benzyl group, a phosphoryl group, or a mercapto group, these groups may optionally having a substituent; $R_4$ and $R_5$ each represent a hydrogen atom, an acyl group, an acetyl group, an amido group, an allyl group, an aryl group, an aldehyde group, a C1 to C6 linear or branched alkyl group, a C1 to C6 alkylene group, a C1 to C6 alkenyl group, a carbamoyl group, a carboxyl group, a cyano group, a sulfo group, a sulfonyl group, a tosyl group, a phenyl group, a benzyl group, or a phosphoryl group, these groups may optionally having a substituent; and the number of repeating units (n) is 1 to 500). The alkyl group of $R_1$ is preferably C1 to C6, more preferably C1 to C4. The alkyl group, alkylene group, alkenyl group, or alkoxy group of $R_2$ or $R_3$ is preferably C1 to C4, more preferably C1 to C3. The alkyl group, alkylene group, or alkenyl group of $R_4$ or $R_5$ is preferably C1 to C4, more preferably C1 to C3. The number of repeating units is preferably 1 to 300, more preferably 1 to 100.

[F7]

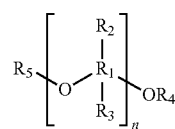

(1)

In the present invention, in formula (2), each of $R_1$, $R_2$, $R_3$, and $R_4$ represents a saturated or unsaturated, linear or branched alkyl or alkenyl group, having a C1 to C10 main chain, the alkyl or alkenyl group having an optional substituent; each of $A_1$ and $A_2$ represents a linear or branched alkylene oxide group having a C2 to C4 main chain (wherein one end (oxygen atom) of the alkylene oxide group is bound to a hydrogen atom, and the other end (carbon atom) is bound to an oxygen atom); and the total number of addition of alkylene oxide units is 0 to 50. The alkyl group or alkenyl group of $R_1$, $R_2$, $R_3$, and $R_4$ is preferably C1 to C8, more preferably C1 to C6. The alkylene oxide group of $A_1$ or $A_2$ is preferably C2 or C3. The number (by mole) of added alkylene oxide units m or n is preferably 0 to 40 in total, more preferably 10 to 30.

[F8]

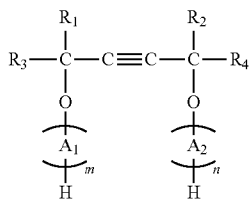

(2)

No particular limitation is imposed on the polyhydric alcohol compound represented by formula (1). Specific examples thereof include dihydric alcohols such as ethyelene glycol (also called 1,2-ethanediol), diethyelene glycol, triethyelene glycol, tetraethyelene glycol, propylene glycol (also called 1,2-propanediol), dipropylene glycol, tripropylene glycol, trimethylene glycol (also called 1,3-propanediol), 1,2-butanediol, 1,3-butanediol, 1,4-butanediol, 2,3-butanediol, 1,2-pentanediol, 1,5-pentanediol, 2,4-pentanediol, hexylene glycol (also called 2-methylpentane-2,4-diol), 1,2-hexanediol, 1,6-hexanediol, 1,2-heptanediol, 1,7-heptanediol, 1,2-octanediol, 1,8-octanediol, 1,2-nonanediol, 1,9-nonanediol, 3-methoxy-1,2-propanediol, 3-(2-ethylhexyloxy)-1,2-propanediol, 3-amino-1,2-propanediol, 3-methylamino-1,2-propanediol, 3-(dimethyl amino)-1,2-propanediol, 3-(diethylamino)-1,2-propanediol, 3-allyloxy-1,2-propanediol, α-chlorohydrin (also called 3-chloro-1,2-propanediol), 3-phenoxy-1,2-propanediol, 3-mercapto-1,2-propanediol, 2-methyl-1,3-propanediol, neopentyl glycol (also called 2,2-dimethyl-1,3-propanediol), 2-methyl-2-propyl-1,3-propanediol, 2-ethyl-2-methyl-1,3-propanediol, 2-butyl-2-ethyl-1,3-propanediol, 2,2-diisobutyl-1,3-propanediol, 2,2-diisopentyl-1,3-propanediol, 2-(2,2-diethoxyethyl)-1,3-propanediol, 2-methylene-1,3-propanediol, serinol (also called 2-amino-1,3-propanediol), 2-amino-2-methyl-1,3-propanediol, 2-amino-2-ethyl-1,3-propanediol, dibromoneopentyl glycol (also called 2,2-bis(bromomethyl)-1,3-propanediol), bronopol (also called 2-bromo-2-nitro-1,3-propanediol), 2-methyl-2-nitro-1,3-propanediol, 2-phenyl-1,3-propanediol, 2-benzyloxy-1,3-propanediol, 3-methyl-1,3-butanediol, 4-benzyloxy-1,3-butanediol, 2,2,3,3-tetrafluoro-1,4-butanediol, pinacol (also called 2,3-dimethyl-2,3-butanediol), DL-1,4-dichloro-2,3-butanediol, 1,4-dimercapto-2,3-butanediol, hexafluoro-2,3-bis(trifluoromethyl)-2,3-butanediol, 2,2,4-trimethyl-1,3-pentanediol, 3-methyl-1,5-pentanediol, 2,4-diethyl-1,5-pentanediol, 2,4-dimethyl-2,4-pentanediol, 2-ethyl-1,3-hexanediol, and 2,5-dimethyl-2,5-hexanediol; trihydric alcohols such as glycerol, diglycerol, 1,2,3-butanetriol, 1,2,4-butanetriol, 1,2,5-pentanetriol, 1,2,6-hexanetriol, 1,2,7-heptanetriol, 1,2,8-octanetriol, 1,2,9-nonanetriol, pentaglycerol (also called 2-hydroxymethyl-2-methyl-1,3-propanediol), trimethylolpropane (also called 2-ethyl-2-hydroxymethyl-1,3-propanediol), Tris base (also called 2-amino-2-(hydroxymethyl)-1,3-propanediol), 2-(bromomethyl)-2-(hydroxymethyl)-1,3-propanediol, and 2-(hydroxymethyl)-2-nitro-1,3-propanediol; ≥4-valent alcohols such as pentaerythritol(also called 2,2-bis(hydroxymethyl)-1,3-propanediol), ditrimethylolpropane (also called 2,2'-oxybis(methylene)bis(2-ethyl-1,3-propanediol)), and L-threitol (also called L-1,2,3,4-butanetetraol); polyalkylene glycols such as polyethyelene glycol, linear or branched polypropylene glycol, polybutylene glycol, polytetramethylene ether glycol, polyoxyethylene-polyoxypropylene glycol, and polyoxyethylene-polyoxypropylene-polyoxyethyelene glycol, wherein the copolymers may be random, alternating, or block; and polyglycerols such as polyoxyethylene glyceryl ether, polyoxypropylene glyceryl ether, polyoxyethylene-polyoxypropylene glyceryl ether, polyoxyethylene-polyoxypropylene trimethylolpropane, polyoxytetramethylene-polyoxyethylene glycol, and polyoxytetramethylene-polyoxypropylene glycol, wherein the copolymers may be random, alternating, or block. Notably, examples further include monomers, dimers, trimers, and the like of the aforementioned polyhydric alcohols. Among them, ethyelene glycol, propylene glycol, dipropylene glycol, tripropylene glycol, 1,3-butanediol, glycerol, pentaerythritol, polyethyelene glycol, and polypropylene glycol are preferred.

No particular limitation is imposed on the derivative of the polyhydric alcohol compound represented by formula (1). Examples thereof include polyhydric alcohol alkyl ethers (polyhydric alcohol ethers) such as ethyelene glycol monomethyl ether, diethyelene glycol monomethyl ether, triethyelene glycol monomethyl ether, ethyelene glycol monoethyl ether, diethyelene glycol monoethyl ether, triethyelene glycol monoethyl ether, ethyelene glycol monopropyl ether, ethyelene glycol monoisopropyl ether, triethyelene glycol monoisopropyl ether, ethyelene glycol monobutyl ether, diethyelene glycol monobutyl ether, triethyelene glycol monobutyl ether, ethyelene glycol monoisobutyl ether, ethyelene glycol mono-tert-butyl ether, diethyelene glycol monohexyl ether, propylene glycol monomethyl ether (also called; propylene glycol 1-monomethyl ether), dipropylene glycol monomethyl ether, tripropylene glycol monomethyl ether, propylene glycol monoethyl ether, propylene glycol monopropyl ether, propylene glycol 1-monobutyl ether, 1,3-propanediolmonomethyl ether, 1,2-butanediol 1-monomethyl ether, 1,4-butanediolmonomethyl ether, ethyelene glycoldimethyl ether, diethyelene glycol dimethyl ether, ethyelene glycol diethyl ether, diethyelene glycol diethyl ether, ethyelene glycol dibutyl ether, diethyelene glycol dibutyl ether, propylene glycol dimethyl ether, dipropylene glycol dimethyl ether, 1,5-pentanediol dimethyl ether, and 1,6-hexanediol dimethyl ether; glycol ethers such as polyethyelene glycol monomethyl ether, polyethyelene glycol dimethyl ether, ethyelene glycol monoacetate, ethyelene glycol monoallyl ether, diethyelene glycolamine (also called; ethyelene glycol mono(2-aminoethyl) ether), ethyelene glycol mono[2-(diethylamino)ethyl] ether, ethyelene glycol monobenzyl ether, diethyelene glycol monoethyl ether acetate, diethyelene glycol monobutyl ether acetate, diethyelene glycol monophenyl ether, diethyelene glycol mono(2-propyn-1-yl) ether, triethyelene glycol monochlorohydrin, triethyelene glycol mono(2-propynyl) ether, triethyelene glycol monobenzyl ether, propylene glycol 1-monomethyl ether 2-acetate, propylene glycol 2-monophenyl ether, ethyelene glycol diacetate, diethyelene glycol diacetate, triethyelene glycol diacetate, ethyelene glycol dichloroacetate, ethyelene glycol ditosylate, diethyelene glycol ditosylate, ethyelene glycol dibutyrate, ethyelene glycol diphenyl ether, ethyelene glycol dibenzyl ether, ethyelene glycol dibenzoate, diethyelene glycol dibenzoate, propylene glycol diacetate, trimethylene glycol ditosylate (also called; 1,3-propanediol ditosylate), neopentyl glycol ditosylate (also called; 2,2-dimethyl 1,3-propanediol ditosylate), 1,4-butanediol diacetate, busulfan (also called; 1,4-butanediol dimethanesulfonate), 1,4-butanediol bis(3-aminopropyl) ether, 1,4-butanediol bis(thioglycolate), 1,5-pentanediol diacetate, 2,5-hexanediol diacetate, 1,8-octanediol diacetate, and 1,9-nonanediol diacetate; polyalkylene glycol alkyl ethers such as polyoxypropylene butyl ether; and polyalkylene glycol ethers such as polyethyelene glycol allyl ether, polyethyelene glycol bis(3-aminopropyl) ether. Among them, propylene glycol 1-monomethyl ether is preferred.

No particular limitation is imposed on the acetylene glycol compound represented by formula (2). Examples thereof include 2-butyne-1,4-diol, 2,5-dimethyl-3-hexyne-2,5-diol, 3,6-dimethyl-4-octyne-3,6-diol, 2,3,6,7-tetramethyl-4-octyne-3,6-diol, 4,7-dimethyl-5-decyne-4,7-diol, 2,4,7,9-tetramethyl-5-decyne-4,7-diol, and 2,5,8,11-tetramethyl-6-dodecyne-5,8-diol.

No particular limitation is imposed on the alkylene oxide adduct of the acetylene glycol compound represented by formula (2). Examples thereof include 3,6-dimethyl-4-octyl-3,6-diol ethylene oxide adduct (ethylene oxide addition (mol); m+n=4), and ethylene oxide derivatives of acetylene glycol such as 2,4,7,9-tetramethyl-5-decyne-4,7-diol ethylene oxide adduct (ethylene oxide addition (mol); m+n=1.3), 2,4,7,9-tetramethyl-5-decyne-4,7-diol ethylene oxide adduct (ethylene oxide addition (mol); m+n=3.5), 2,4,7,9-tetramethyl-5-decyne-4,7-diol ethylene oxide adduct (ethylene oxide addition (mol); m+n=10), 2,4,7,9-tetramethyl-5-decyne-4,7-diol ethylene oxide adduct (ethylene oxide addition (mol); m+n=30), and 2,5,8,11-tetramethyl-6-dodecyne-5,8-diol ethylene oxide adduct (ethylene oxide addition (mol); m+n=6). Among them, 2,4,7,9-tetramethyl-5-decyne-4,7-diol ethylene oxide adduct (ethylene oxide addition (mol); m+n=10), 2,4,7,9-tetramethyl-5-decyne-4,7-diol ethylene oxide adduct (ethylene oxide addition (mol); m+n=30), and the like are particularly preferred.

Commercial products of the acetylene glycol compound and the alkylene oxide adduct thereof include Surfynol series and Olfine series (products of Nissin Chemical Industry Co., Ltd.) and Acetylenol series (products of Kawaken Fine Chemicals Co., Ltd.).

Compounds (A) represented by formulas (1) and (2) may be used singly or in combination of two or more species.

The saccharification reaction mixture of the present invention contains at least one of cellulose and hemicellulose as a source, and a saccharification enzyme composition containing a saccharification enzyme, silica or a silica-containing substance, and at least one compound (A) selected from the group consisting of a polyhydric alcohol compound represented by the following formula (1) or a derivative thereof and an acetylene glycol represented by formula (2) or an alkylene oxide adduct thereof. From the viewpoint of enjoying the effect of enhancing saccharification reaction efficiency (also referred to simply as reaction efficiency), the saccharification reaction mixture preferably contains silica or a silica-containing substance in combination with compound (A). Details of this will be described in another paragraph.

In the saccharification reaction mixture, the saccharification enzyme concentration is 0.001 mass % to 3.0 mass %, as calculated to BSA (bovine serum albumin) protein concentration, preferably 0.001 mass % to 1.0 mass %. When the saccharification enzyme concentration is lower than 0.001 mass %, reaction efficiency is disadvantageously poor, whereas when the saccharification enzyme concentration is higher than 3.0 mass %, dissolution of the saccharification enzyme is impeded, and cost disadvantageously increases.

In the saccharification reaction mixture, the silica concentration or the silica concentration of the silica-containing substance is 0.001 mass % to 40 mass %, preferably 0.005 mass % to 10 mass %. When the silica concentration or the silica concentration of the silica-containing substance is lower than 0.001 mass %, reaction efficiency is disadvantageously poor, whereas when the colloidal silica concentration is higher than 40 mass %, dispersibility is poor, and cost disadvantageously increases.

In the saccharification reaction mixture, the ratio by mass of the saccharification enzyme to silica (or silica of the silica-containing substance (saccharification enzyme/silica) is 0.0002 to 300, preferably 0.002 to 30. When the (saccharification enzyme/silica) mass ratio falls outside the range, considerable enhancement in reaction efficiency fails to be attained.

In the saccharification reaction mixture, the compound (A) concentration is 0.00001 mass % to 10 mass %, preferably 0.0001 mass % to 1 mass %. When the compound (A) concentration is lower than 0.00001 mass %, reaction efficiency is disadvantageously poor, whereas when the compound (A) concentration is higher than 10 mass %, dispersibility is impeded, and cost disadvantageously increases.

In the saccharification reaction mixture, the ratio by mass of compound (A) to silica (or silica of the silica-containing substance (compound (A)/silica) is 0.0001 to 1, preferably 0.001 to 0.1. When the (compound (A)/silica) mass ratio falls outside the range, considerable enhancement in reaction efficiency fails to be attained.

The pH of the saccharification reaction mixture is 3 to 11, preferably 3 to 6. When the pH is lower than 3, the reaction efficiency of the saccharification enzyme is lowered due to aggregation of silica or a silica-containing substance, whereas when the pH is higher than 11, undesired dissolution of colloidal silica or a silica-containing substance tends to occur. Both cases are not preferred.

Examples of the pH-adjusting agent for the saccharification reaction mixture include mineral acids such as sulfuric acid, hydrochloric acid, and nitric acid; carboxylic acids such as acetic acid and oxalic acid; hydroxyacids such as citric acid, tartaric acid, and malic acid; hydroxide salts such as sodium hydroxide and potassium hydroxide; ammonia; and urea. No particular limitation is imposed on the type and concentration of the pH-adjusting agent, so long as the effects of the present invention are not impaired. Also, these pH-adjusting agents may be used singly or in combination of two or more species. Furthermore, the pH-adjusting agent may be used in a buffer having a buffering action.

The reaction temperature of the saccharification reaction mixture of the present invention is preferably 5° C. to 100° C., more preferably 20° C. to 55° C. The reaction temperature is preferably adjusted so as to fit to the optimum temperature of the saccharification enzyme. Generally, when the reaction temperature is lower than 5° C., saccharization efficiency considerably decreases, whereas when the reaction temperature is higher than 100° C., the saccharification enzyme may be deactivated. Both cases are not preferred.

Notably, the cellulosic biomass materials containing cellulose or hemicellulose may be preliminarily treated in a known manner. Generally, the biomass material may be subjected to physical crushing by means of a cutter mill or the like, an acid or alkaline treatment for chemically destructing the structures of lignin, cellulose, and hemicellulose, to thereby provide a raw material to be saccharified.

In preparation of the saccharification reaction mixture, silica or a silica-containing substance and compound (A) may be added to the reaction mixture in which the saccharification enzyme is dispersed. Alternatively, a saccharification enzyme may be added to the reaction mixture in which silica or a silica-containing substance and compound (A) are dispersed. Silica or the silica-containing substance and compound (A) may be added simultaneously or separately. No particular limitation is imposed on the order of addition, so long as the saccharification reaction efficiency does not decrease. Upon addition, compound (A) in the powder or liquid form may be used. Also, so long as the effects of the present invention are not impaired, the pH-adjusting agent and other additives may be added in any order.

As described above, the saccharification reaction mixture of the present invention is produced from at least one of cellulose and hemicellulose as a source, and a saccharification enzyme composition containing a saccharification enzyme, silica, and at least one compound (A) selected from the group consisting of a polyhydric alcohol compound represented by the following formula (1) or a derivative thereof and an acetylene glycol represented by formula (2) or an alkylene oxide adduct thereof. Although no precise mechanism has been elucidated, when silica or the silica-containing substance and compound (A) are used in combination in the saccharification reaction mixture, saccharification of cellulose or hemicellulose can be further promoted.

In addition, since the saccharification reaction mixture of the present invention uses silica or a silica-containing substance in combination with compound (A), the amount of saccharification enzyme can be reduced, which is preferred in terms of cost.

The saccharide produced in the present invention may be subjected to ethanol fermentation in the presence of a microorganism which can cause fermentation, to thereby produce ethanol. Alternatively, after production of a saccharide, the fermentation microorganism which can cause ethanol fermentation may be added, to thereby carry out ethanol fermentation, whereby ethanol is produced. Yet alternatively, the fermentation microorganism which can cause ethanol fermentation may be added to a sugar production step employing the saccharification reaction mixture, to thereby simultaneously carry out sugar production and ethanol fermentation, whereby ethanol is produced.

Examples of the fermentation microorganism of the present invention include a yeast, a mold, and a bacterium. Among them, a yeast or a bacterium are preferred. These fermentation microorganisms may be used singly or in combination of two or more species. Specific examples of the fermentation microorganism include a microorganism belonging to the *Saccharomyces,* a microorganism belonging to the *Zymomonas,* a microorganism belonging to the *Pichia,* a microorganism belonging to the *Candida,* a microorganism belonging to the *Zymobacter,* a microorganism belonging to the *Corynebacterium,* a microorganism belonging to the *Kluyveromyces,* or a microorganism belonging to the *Escherichia.*

The temperature at which ethanol fermentation is carried out is preferably 15° C. to 35° C., more preferably 28° C. to 32° C. Generally, when the fermentation temperature is lower than 15° C., the fermentation microorganism is less active, thereby considerably reducing the efficiency of ethanol fermentation, whereas when the fermentation temperature is higher than 35° C., the fermentation microorganism may be killed. Both cases are not preferred.

In ethanol production of the present invention, including ethanol fermentation by use of a fermentation microorganism, silica or a silica-containing substance is employed in combination with compound (A). Therefore, a target saccharide can be produced by a saccharification enzyme at high efficiency, even at a fermentation temperature suitable for ethanol fermentation. Thus, ethanol fermentation of the produced saccharide can also be carried out at high efficiency. Generally, since the reaction temperature for producing saccharide is higher than the fermentation temperature for producing ethanol, the reaction mixture must be cooled before the ethanol fermentation step, resulting in undesired waste in energy. However, according to the effective method of the present invention, the reaction temperature for producing saccharide and the fermentation temperature for producing ethanol may be adjusted to fall within the same range, thereby avoiding waste of energy.

EXAMPLES

The present invention will next be described in more detail by way of examples, which should not be construed as limiting the invention thereto.

[1. Production of Saccharide by Use of Silica as "Silica or Silica-Containing Substance"]
(1-1. Mean Primary Particle Size)

The mean primary particle size of silica particles was measured by means of the following apparatus.

Apparatus in nitrogen adsorption method: Monosorb MS-16 (product of Quantachrome Instruments Japan),
(1-2. Cellulase Aqueous Solution)

A cellulase aqueous solution was produced through the following procedure.

A powder of a cellulase mixture having a specific component ratio was added to deionized water, and the mixture was stirred at room temperature by means of a rotor which was rotated at 100 rpm for 30 minutes, to thereby prepare a cellulase aqueous solution. The cellulase mixture serving as a saccharification enzyme was a mixture (7:3 (w/w)) of a cellulase originating from the *Trichoderma reesei* (*T. reesei*) (product of Sigma Aldrich) and a cellulase originating from the *Aspergillus niger* (*A. niger*) (product of MP Biomedicals). The cellulase mixture exhibits an optimum enzymatic activity within a pH range of 3 to 6.
(1-3. Saccharification Enzyme Aqueous Solutions)

Saccharification enzyme aqueous solutions were produced through the following procedure.

To deionized water, 1M acetate buffer (for adjusting pH to 5.0) and the cellulase aqueous solution prepared in 1-2. were added, so that the buffer concentration was adjusted to 0.05 M. The mixture was stirred at room temperature by means of a rotor which was rotated at 100 rpm for 30 minutes, to thereby prepare saccharification enzyme aqueous solutions having a saccharification enzyme concentration (cellulase concentration in the Examples) shown in Table 1. These saccharification enzyme aqueous solutions were employed as comparative samples 1 to 3. The saccharification enzyme concentration was calculated as a BSA (protein standard substance, product of Sigma Aldrich) protein concentration based on the Bradford method (CBB method). The specific procedure is as follows.

A protein assay CBB solution (5-fold concentrated) (product of Nacalai Tesque) was 5-fold diluted with deionized water. To a disposable cell (cell path length: 10 mm), the diluted CBB solution (2.5 mL) and each of the comparative samples 1 to 3 (0.05 mL) were sequentially added. The disposable cell was tightly closed, and the contents were uniformly mixed in an up and down manner repeatedly. Thereafter, the mixture was allowed to stand for 30 minutes, and the absorbance of the sample was measured at 595 nm wavelength by means of a spectrophotometer UV-3150 (product of Shimadzu Corporation). A calibration curve was drawn from absorbance measurements obtained in the same manner from BSA protein concentration-known samples. The saccharification enzyme concentration of the sample was calculated by the thus-drawn calibration curve. Notably, a powder (1 g) of the cellulase derived from the *Trichoderma reesei* was found to contain 0.27 g of protein. Also, a powder (1 g) of the cellulase derived from the *Aspergillus niger* was found to contain 0.06 g of protein.

Table 1

| Saccharification enzyme aqueous soln. | Cellulase from | Cellulase concn. mass % | pH |
|---|---|---|---|
| comp. sample 1 | *T. reesei* / *A. niger* | 0.003 | 5.0 |
| comp. sample 2 | *T. reesei* / *A. niger* | 0.004 | 5.0 |
| comp. sample 3 | *T. reesei* / *A. niger* | 0.005 | 5.0 |

(1-4. Saccharification Enzyme Composition)

Saccharification enzyme compositions were prepared through the following procedure.

To deionized water, 1M acetate buffer (for adjusting pH to 5.0), silica, compound (A), and the cellulase aqueous solution prepared in 1-2. were added, so that the buffer concentration was adjusted to 0.05 M. The silica was an acidic silica sol (pH: 2.1, silica concentration: 40 mass %) containing dense spherical colloidal silica (mean primary particle size: 35 nm) produced through the water glass method and dispersed in water, and compound (A) was tripropylene glycol. The mixture was stirred at room temperature by means of a rotor which was rotated at 100 rpm for 30 minutes, to thereby prepare saccharification enzyme compositions having a saccharification enzyme concentration (cellulase concentration in the Examples), silica concentration, and compound (A) concentration, shown in Table 2. These saccharification enzyme compositions were employed as samples 1 to 8. Notably, in Table 2, the component concentration of each of samples 1 to 8 represents the corresponding concentration of the saccharification enzyme composition.

Furthermore, the procedure of preparing samples 1 to 8 was repeated, except that a polyhydric alcohol compound, a polyhydric alcohol compound derivative, or an acetylene glycol alkylene oxide adduct was used as compound (A), to thereby prepare different saccharification enzyme compositions. These saccharification enzyme compositions were employed as samples 9 to 20 shown in Table 2. Notably, in Table 2, the component concentration of each of samples 9 to 20 represents the corresponding concentration of the saccharification enzyme composition.

In Table 2, symbols A to M of compound (A) are as follows:
A: tripropylene glycol
B: ethyelene glycol
C: polyethyelene glycol (average molecular weight: 200)
D: propylene glycol
E: dipropylene glycol
F: polypropylene glycol (average molecular weight: 250)
G: polypropylene glycol (average molecular weight: 700)
H: polypropylene glycol (average molecular weight: 1,000)
I: propylene glycol monomethyl ether
J: 1,3-butanediol
K: glycerin
L: 2,4,7,9-tetramethyl-5-decyne-4,7-diol ethylene oxide adduct (ethylene oxide addition (mol); m+n=10) (Surfynol 465, product of Nissin Chemical Industry Co., Ltd.)
M: 2,4,7,9-tetramethyl-5-decyne-4,7-diol ethylene oxide adduct (ethylene oxide addition (mol); m+n=30) (Surfynol 485, product of Nissin Chemical Industry Co., Ltd.)

TABLE 2

| samples | Cellulase from | Cellulase concn. mass % | Silica sol Mean primary particle size nm | Silica concn. mass % | compd. (A) Type | compd. (A) concn. mass % | compd. (A)/ silica wt. ratio | pH |
|---|---|---|---|---|---|---|---|---|
| 1 | *T. reesei* & *A. niger* | 0.003 | 35 | 1 | A | 1 | 1 | 5.0 |
| 2 | *T. reesei* & *A. niger* | 0.003 | 35 | 1 | A | 0.5 | 0.5 | 5.0 |
| 3 | *T. reesei* & *A. niger* | 0.003 | 35 | 1 | A | 0.1 | 0.1 | 5.0 |
| 4 | *T. reesei* & *A. niger* | 0.003 | 35 | 1 | A | 0.01 | 0.01 | 5.0 |
| 5 | *T. reesei* & *A. niger* | 0.003 | 35 | 1 | A | 0.001 | 0.001 | 5.0 |
| 6 | *T. reesei* & *A. niger* | 0.003 | 35 | 1 | A | 0.0001 | 0.0001 | 5.0 |
| 7 | *T. reesei* & *A. niger* | 0.004 | 35 | 1 | A | 0.1 | 0.1 | 5.0 |
| 8 | *T. reesei* & *A. niger* | 0.005 | 35 | 1 | A | 0.1 | 0.1 | 5.0 |
| 9 | *T. reesei* & *A. niger* | 0.003 | 35 | 1 | B | 0.1 | 0.1 | 5.0 |
| 10 | *T. reesei* & *A. niger* | 0.003 | 35 | 1 | C | 0.1 | 0.1 | 5.0 |
| 11 | *T. reesei* & *A. niger* | 0.003 | 35 | 1 | D | 0.1 | 0.1 | 5.0 |
| 12 | *T. reesei* & *A. niger* | 0.003 | 35 | 1 | E | 0.1 | 0.1 | 5.0 |
| 13 | *T. reesei* & *A. niger* | 0.003 | 35 | 1 | F | 0.1 | 0.1 | 5.0 |
| 14 | *T. reesei* & *A. niger* | 0.003 | 35 | 1 | G | 0.1 | 0.1 | 5.0 |
| 15 | *T. reesei* & *A. niger* | 0.003 | 35 | 1 | H | 0.1 | 0.1 | 5.0 |
| 16 | *T. reesei* & *A. niger* | 0.003 | 35 | 1 | I | 0.1 | 0.1 | 5.0 |
| 17 | *T. reesei* & *A. niger* | 0.003 | 35 | 1 | J | 0.1 | 0.1 | 5.0 |
| 18 | *T. reesei* & *A. niger* | 0.003 | 35 | 1 | K | 0.1 | 0.1 | 5.0 |
| 19 | *T. reesei* & *A. niger* | 0.003 | 35 | 1 | L | 0.1 | 0.1 | 5.0 |
| 20 | *T. reesei* & *A. niger* | 0.003 | 35 | 1 | M | 0.1 | 0.1 | 5.0 |

(1-5. Saccharification Enzyme Aqueous Solutions Containing Tripropylene Glycol)

Saccharification enzyme aqueous solutions containing tripropylene glycol as compound (A) were prepared through the following procedure.

To deionized water, 1M acetate buffer (for adjusting pH to 5.0), tripropylene glycol, and the cellulase aqueous solution prepared in 1-2. were added, so that the buffer concentration was adjusted to 0.05 M. The mixture was stirred at room temperature by means of a rotor which was rotated at 100 rpm for 30 minutes, to thereby prepare tripropylene glycol-containing saccharification enzyme aqueous solutions having a saccharification enzyme concentration (cellulase concentration in the Examples) and tripropylene glycol concentration shown in Table 3. These tripropylene glycol-containing saccharification enzyme aqueous solutions were employed as comparative samples 4 to 11. Notably, in Table 3, the component concentration of each of comparative samples 4 to 11 represents the corresponding concentration of the tripropylene glycol-containing saccharification enzyme aqueous solution.

TABLE 3

| TPG-containing saccharification enzyme aqueous soln. | Cellulase | | Tripropylene glycol TPG concn. mass % | pH |
|---|---|---|---|---|
| | Cellulase from | Cellulase concn. mass % | | |
| comp. sample 4 | T. reesei A. niger | 0.003 | 1 | 5.0 |
| comp. sample 5 | T. reesei A. niger | 0.003 | 0.5 | 5.0 |
| comp. sample 6 | T. reesei A. niger | 0.003 | 0.1 | 5.0 |
| comp. sample 7 | T. reesei A. niger | 0.003 | 0.01 | 5.0 |
| comp. sample 8 | T. reesei A. niger | 0.003 | 0.001 | 5.0 |
| comp. sample 9 | T. reesei A. niger | 0.003 | 0.0001 | 5.0 |
| comp. sample 10 | T. reesei A. niger | 0.004 | 0.1 | 5.0 |
| comp. sample 11 | T. reesei A. niger | 0.005 | 0.1 | 5.0 |

(1-6. Saccharification Enzyme Aqueous Solution Containing Silica)

Silica-containing saccharification enzyme aqueous solutions were prepared through the following procedure.

To deionized water, 1M acetate buffer (for adjusting pH to 5.0), silica, and the cellulase aqueous solution prepared in 1-2. were added, so that the buffer concentration was adjusted to 0.05 M. The silica was an acidic silica sol (pH: 2.1, silica concentration: 40 mass %) containing dense spherical colloidal silica (mean primary particle size: 35 nm) produced through the water glass method and dispersed in water. The mixture was stirred at room temperature by means of a rotor which was rotated at 100 rpm for 30 minutes, to thereby yield silica-containing saccharification enzyme aqueous solutions having a saccharification enzyme concentration (cellulase concentration in the Examples) and silica concentration shown in Table 4. These silica-containing saccharification enzyme aqueous solutions were employed as comparative samples 12 to 14. Notably, in Table 4, the component concentration of each of comparative samples 12 to 14 represents the corresponding concentration of the silica-containing saccharification enzyme aqueous solution.

TABLE 4

| Silica-containing saccharification enzyme aqueous soln. | Cellulase | | Silica | | pH |
|---|---|---|---|---|---|
| | Cellulase from | Cellulase concn. mass % | Mean primary particle size nm | Silica concn. mass % | |
| comp. sample 12 | T. reesei A. niger | 0.003 | 35 | 1 | 5.0 |
| comp. sample 13 | T. reesei A. niger | 0.004 | 35 | 1 | 5.0 |
| comp. sample 14 | T. reesei A. niger | 0.005 | 35 | 1 | 5.0 |

(1-7. Saccharification Reaction Mixture)

To each of the saccharification enzyme compositions of samples 1 to 20, microcrystalline cellulose powder was added. The powder was dispersed in the composition, to thereby prepare a saccharification reaction mixture employing the corresponding sample. The specific procedure is as follows.

Firstly, each sample (10 mL) was placed in a glass bottle (capacity: 13.5 mL). While the contents were stirred by means of a stirrer (4 mmϕ×10 mm length), microcrystalline cellulose powder (crystal type: I, Avicel PH-101, product of Sigma Aldrich) was added in an amount of 0.05 g (equivalent to 5 mg/mL). Then, the bottle was tightly closed with a stopper.

Also, the procedure of preparing the saccharification enzyme compositions of samples 1 to 20 was repeated, except that saccharification enzyme aqueous solutions (comparative samples 1 to 3), tripropylene glycol-containing saccharification enzyme aqueous solutions (comparative samples 4 to 11), and silica-containing saccharification enzyme aqueous solutions (comparative samples 12 to 14) were used, to thereby yield the corresponding saccharification reaction mixtures of comparative samples.

(1-8. Production of Saccharide)

A saccharification reaction mixture employing each of the aforementioned samples and comparative samples was caused to be reacted enzymatically in a thermostatic bath (25° C.) under stirring for two days, to thereby form a saccharide (glucose).

(1-9. Calculation of Glucose Formation Amount)

Example 1

The saccharification reaction mixture obtained from the saccharification enzyme composition of sample 1 (hereinafter, the reaction mixture will be referred to as "saccharification reaction mixture of Example 1") was subjected to enzymatic reaction (1-8.). Two days after the enzymatic reaction, the amount of formed glucose was calculated through an enzymatic method (GOD method).

A saccharification reaction mixture (sample 1) (0.5 mL) was sampled into a microtube (2 mL), and the enzyme in the tube was deactivated at 105° C. for 15 minutes. Then, the reaction mixture was transferred to a microtube (2 mL) equipped with a filter (absolute pore size: 0.1 μm), so as to remove unreacted cellulose and silica. The mixture was centrifuged means of a high speed refrigerated centrifuge SRX-201 (product of Tomy Seiko Co., Ltd.) at 10,000 G for 5 minutes, and the supernatant was recovered. In the GOD method, Glucose CII-Test Wako (product of Wako Pure Chemical Industries, Ltd.) was used. The absorbance of the sample was measured at 505 nm (cell path length: 10 mm)

by means of a spectrophotometer UV-3150 (product of Shimadzu Corporation). The specific procedure is as follows.

To a disposable cell (cell path length: 10 mm), a coloring agent (liquid) (3.0 mL) and the aforementioned supernatant (0.02 mL) were sequentially added. The disposable cell was tightly closed, and the contents were uniformly mixed in an up and down manner repeatedly. Thereafter, the mixture was allowed to stand at 24° C. for 15 minutes, and the absorbance of the sample was measured at 505 nm by means of a spectrophotometer (the absorbance: Es). Separately, to another disposable cell (cell path length: 10 mm), a coloring agent (liquid) (3.0 mL) and 500-mg/dL glucose standard liquid II (0.02 mL) were sequentially added. The disposable cell was tightly closed, and the contents were uniformly mixed in an up and down manner repeatedly. Thereafter, the mixture was allowed to stand at 24° C. for 15 minutes, and the absorbance of the sample was measured at 505 nm by means of a spectrophotometer (the absorbance: Estd). In this measurement procedure, the absorbance of the saccharification reaction mixture of Example 1 (Es) and that of glucose standard liquid II (Estd) were measured with respect to the absorbance of the coloring agent (liquid) 3.0 mL as a reference sample.

Next, the amount (mg/mL) of formed glucose from the saccharification reaction mixture of Example 1 was determined by the following formula (3). Table 5 shows the results.

[MF1]

$$\text{Glucose formation amount}=(Es/Estd)\times 5 \quad (3)$$

Examples 2 to 20

In the same manner as employed in Example 1, the saccharification reaction mixtures obtained from the saccharification enzyme compositions of samples 2 to 20 (hereinafter, the reaction mixtures will be referred to as "saccharification reaction mixtures of Examples 2 to 20") were subjected to enzymatic reaction (1-8.). Two days after the enzymatic reaction, the amount of formed glucose from each mixture was calculated. Table 5 shows the results.

TABLE 5

| | | Enzym. reaction conditions | | | |
|---|---|---|---|---|---|
| | Saccharification enzyme compn. | Cellulose concn. mg/mL | Reaction temp. ° C. | Reaction time day | Glucose amount mg/mL |
| Ex. 1 | sample 1 | 5 | 25 | 2 | 3.37 |
| Ex. 2 | sample 2 | 5 | 25 | 2 | 3.35 |
| Ex. 3 | sample 3 | 5 | 25 | 2 | 3.40 |
| Ex. 4 | sample 4 | 5 | 25 | 2 | 3.36 |
| Ex. 5 | sample 5 | 5 | 25 | 2 | 3.35 |
| Ex. 6 | sample 6 | 5 | 25 | 2 | 3.20 |
| Ex. 7 | sample 7 | 5 | 25 | 2 | 3.56 |
| Ex. 8 | sample 8 | 5 | 25 | 2 | 3.88 |
| Ex. 9 | sample 9 | 5 | 25 | 2 | 3.21 |
| Ex. 10 | sample 10 | 5 | 25 | 2 | 3.34 |
| Ex. 11 | sample 11 | 5 | 25 | 2 | 3.27 |
| Ex. 12 | sample 12 | 5 | 25 | 2 | 3.44 |
| Ex. 13 | sample 13 | 5 | 25 | 2 | 3.54 |
| Ex. 14 | sample 14 | 5 | 25 | 2 | 3.76 |
| Ex. 15 | sample 15 | 5 | 25 | 2 | 3.81 |
| Ex. 16 | sample 16 | 5 | 25 | 2 | 3.27 |
| Ex. 17 | sample 17 | 5 | 25 | 2 | 3.29 |
| Ex. 18 | sample 18 | 5 | 25 | 2 | 3.35 |
| Ex. 19 | sample 19 | 5 | 25 | 2 | 3.87 |
| Ex. 20 | sample 20 | 5 | 25 | 2 | 3.51 |

Comparative Examples 1 to 14

In the same manner as employed in Example 1, the saccharification reaction mixtures obtained from the saccharification enzyme aqueous solution of comparative samples 1 to 3, the tripropylene glycol-containing saccharification enzyme aqueous solution of comparative samples 4 to 11, and the silica-containing saccharification enzyme aqueous solution of comparative samples 12 to 14 (hereinafter, the reaction mixtures will be referred to as "saccharification reaction mixtures of Comparative Examples 1 to 14") were subjected to enzymatic reaction (1-8.). Two days after the enzymatic reaction, the amount of formed glucose from each mixture was calculated. Table 6 shows the results.

TABLE 6

| | | | Enzym. reaction conditions | | |
|---|---|---|---|---|---|
| Comp. Exs. | Saccharification enzyme aq. solns. | | Cellulose concn. mg/mL | Reaction temp. ° C. | Reaction time day | Glucose amount mg/mL |
| Comp. 1 | Saccharification enzyme aq. soln. | comp. sample 1 | 5 | 25 | 2 | 2.95 |
| Comp. 2 | Saccharification enzyme aq. soln. | comp. sample 2 | 5 | 25 | 2 | 3.13 |
| Comp. 3 | Saccharification enzyme aq. soln. | comp. sample 3 | 5 | 25 | 2 | 3.32 |
| Comp. 4 | TPG-containing saccharification enzyme aq. soln. | comp. sample 4 | 5 | 25 | 2 | 2.62 |
| Comp. 5 | TPG-containing saccharification enzyme aq. soln. | comp. sample 5 | 5 | 25 | 2 | 2.70 |
| Comp. 6 | TPG-containing saccharification enzyme aq. soln. | comp. sample 6 | 5 | 25 | 2 | 2.80 |
| Comp. 7 | TPG-containing saccharification enzyme aq. soln. | comp. sample 7 | 5 | 25 | 2 | 2.81 |
| Comp. 8 | TPG-containing saccharification enzyme aq. soln. | comp. sample 8 | 5 | 25 | 2 | 2.95 |
| Comp. 9 | TPG-containing saccharification enzyme aq. soln. | comp. sample 9 | 5 | 25 | 2 | 2.92 |
| Comp. 10 | TPG-containing saccharification enzyme aq. soln. | comp. sample 10 | 5 | 25 | 2 | 2.97 |
| Comp. 11 | TPG-containing saccharification enzyme aq. soln. | comp. sample 11 | 5 | 25 | 2 | 3.23 |

TABLE 6-continued

| | | | Enzym. reaction conditions | | | |
|---|---|---|---|---|---|---|
| Comp. Exs. | Saccharification enzyme aq. solns. | | Cellulose concn. mg/mL | Reaction temp. °C | Reaction time day | Glucose amount mg/mL |
| Comp. 12 | Silica-containing saccharification enzyme aq. soln. | comp. sample 12 | 5 | 25 | 2 | 3.08 |
| Comp. 13 | Silica-containing saccharification enzyme aq. soln. | comp. sample 13 | 5 | 25 | 2 | 3.46 |
| Comp. 14 | Silica-containing saccharification enzyme aq. soln. | comp. sample 14 | 5 | 25 | 2 | 3.66 |

(1-10. Saccharification Reaction Efficiency)

Saccharification reaction efficiency of each saccharification reaction mixture was assessed on the basis of the glucose formation amount shown in Table 5 or 6. Firstly, from the glucose formation amounts obtained in Examples 3, 7, and 8, and Comparative Examples 1 to 3, 6, and 10 to 14, the effect of tripropylene glycol addition on enhancement in saccharification reaction efficiency was investigated.

FIG. 1 is a graph showing enhancement in saccharification reaction efficiency through addition of tripropylene glycol (Examples 3, 7, and 8, and Comparative Examples 1 to 3, 6, and 10 to 14). As shown in FIG. 1, in comparison of saccharification reaction mixtures of Comparative Examples 1 to 3 with those of Comparative Examples 12 to 14, saccharification reaction mixtures of Comparative Examples 12 to 14, prepared by adding silica to the corresponding cellulase aqueous solution, exhibited larger glucose formation amounts, indicating enhancement in saccharification reaction efficiency. In comparison of saccharification reaction mixtures of Comparative Examples 12 to 14 with those of Examples 3, 7, and 8, saccharification reaction mixtures of Examples 3, 7, and 8, prepared by adding silica and tripropylene glycol to the corresponding cellulase aqueous solution, exhibited larger glucose formation amounts, indicating enhancement in saccharification reaction efficiency. In contrast, in comparison of saccharification reaction mixtures of Comparative Examples 1 to 3 with those of Comparative Examples 6, 10, and 11, even when tripropylene glycol was added to the corresponding cellulase aqueous solution, no effect of enhancing saccharification reaction efficiency was observed. Therefore, in cellulose saccharification reaction, enhancement in saccharification reaction efficiency was confirmed through combination use of silica and tripropylene glycol.

Furthermore, in terms of the amount of cellulase, saccharification reaction mixtures of Comparative Examples 1 to 3 were compared with those of Comparative Examples 12 to 14, prepared by adding silica to the corresponding cellulase aqueous solution. As a result, the amount of cellulase was reduced at about 20%, when any of the saccharification reaction mixtures of Comparative Examples 12 to 14 was used. Also, in terms of the amount of cellulase, saccharification reaction mixtures of Comparative Examples 1 to 3 were compared with those of Examples 3, 7, and 8, prepared by adding silica and tripropylene glycol to the corresponding cellulase aqueous solution. As a result, the amount of cellulase can be expected to be reduced at about 30%, when any of the saccharification reaction mixtures of Examples 3, 7, and 8 is used. As compared with the case where silica was added to the corresponding cellulase aqueous solution, the amount of cellulase used in saccharification reaction is thought to be further reduced by about 10%.

Next, the effect of the amount of tripropylene glycol addition (i.e., tripropylene glycol concentration) on enhancement in saccharification reaction efficiency was investigated, from the glucose formation amounts obtained in Examples 1 to 6, and Comparative Examples 1, 4 to 9, and 12.

FIG. 2 is a graph showing enhancement in saccharification reaction efficiency, with respect to tripropylene glycol concentration (Examples 1 to 6, and Comparative Examples 1, 4 to 9, and 12). As shown in FIG. 2, when the ratio by mass of tripropylene glycol to silica (tripropylene glycol/silica) was about 0.0001 to about 1, saccharification reaction efficiency was remarkably enhanced, confirming the effect of combination use of tripropylene glycol and silica. Therefore, the glucose formation amount was suggested to depend particularly on the amount of tripropylene glycol added. Note that when only tripropylene glycol was added to the saccharification enzyme (cellulase), no effect of enhancing saccharification reaction efficiency was observed.

Also, from the glucose formation amounts obtained in Examples 9 to 20, and Comparative Examples 1 and 12, the effect of addition of compound (A) other than tripropylene glycol (i.e., a polyhydric alcohol compound, a polyhydric alcohol compound derivative, or an acetylene glycol alkylene oxide adduct) on enhancement in saccharification reaction efficiency was investigated.

FIG. 3 is a graph showing enhancement in saccharification reaction efficiency through addition of a polyhydric alcohol compound, a polyhydric alcohol compound derivative, or an acetylene glycol alkylene oxide adduct (Examples 9 to 20, and Comparative Examples 1 and 12). As shown in FIG. 3, in comparison of saccharification reaction mixtures of Examples 9 to 20 with those of Comparative Examples 1 and 12, the effect of enhancement in saccharification reaction efficiency was observed in saccharification reaction mixtures of Examples 9 to 20, prepared by adding silica with a polyhydric alcohol compound, a polyhydric alcohol compound derivative, or an acetylene glycol alkylene oxide adduct, to the corresponding cellulase aqueous solution. As a result, when silica was used with a polyhydric alcohol compound, a polyhydric alcohol compound derivative, or an acetylene glycol alkylene oxide adduct, as compound (A), in cellulose saccharification reaction, enhancement in saccharification reaction efficiency was confirmed.

[2. Production of Saccharide by Use Commercial Cellulase]
(2-1. Cellulase Aqueous Solution)

The procedure of 1-2. was repeated, except that a commercial cellulase (Cellic (registered trademark) CTec2, product of Novozymes) was used instead of a mixture (7:3 (w/w)) of a cellulase originating from the *T. reesei* (product of Sigma Aldrich) and a cellulase originating from the *A. niger* (product of MP Biomedicals), to thereby prepare cellulase aqueous solution.

(2-2. Saccharification Enzyme Composition)

A saccharification enzyme composition was produced through the following procedure.

To deionized water, 1M acetate buffer (for adjusting pH to 5.0), silica, compound (A), and the cellulase aqueous solution prepared in 2-1. were added, so that the buffer concentration was adjusted to 0.05 M. The silica was an alkaline silica sol (pH: 9.3, silica concentration: 40 mass %) containing dense spherical colloidal silica (mean primary particle size: 85 nm) produced through the water glass method and dispersed in water, and compound (A) was polypropylene glycol (average molecular weight: 1,000) (hereinafter referred to as PPG 1000). The mixture was stirred at room temperature by means of a rotor which was rotated at 100 rpm for 30 minutes, to thereby prepare a saccharification enzyme composition having a saccharification enzyme concentration (cellulase concentration in the Example), silica concentration, and PPG 1000 concentration, shown in Table 7. The saccharification enzyme composition was employed as sample 21. Notably, in Table 7, the component concentration of sample 21 represents the corresponding concentration of the saccharification enzyme composition.

(2-3. Saccharification Enzyme Aqueous Solution)

A saccharification enzyme composition was produced through the following procedure.

To deionized water, 1M acetate buffer (for adjusting pH to 5.0), silica and the aforementioned cellulase aqueous solutions were added, so that the buffer concentration was adjusted to 0.05 M. The mixture was stirred at room temperature by means of a rotor which was rotated at 100 rpm for 30 minutes, to thereby prepare a saccharification enzyme aqueous solution having a saccharification enzyme concentration (cellulase concentration in the Example) shown in Table 7. The saccharification enzyme aqueous solution was employed as comparative sample 15.

(2-4. Saccharification Enzyme Aqueous Solution Containing Polypropylene Glycol)

Through the following procedure, a saccharification enzyme aqueous solution containing PPG 1000 was prepared by use of the same PPG 1000 employed in 2-2. as compound (A).

To deionized water, 1M acetate buffer (for adjusting pH to 5.0), PPG 1000, and the cellulase aqueous solutions prepared in 2-1. were added, so that the buffer concentration was adjusted to 0.05 M. The mixture was stirred at room temperature by means of a rotor which was rotated at 100 rpm for 30 minutes, to thereby prepare a PPG 1000-containing saccharification enzyme aqueous solution having a saccharification enzyme concentration (cellulase concentration in the Example) and PPG 1000 concentration shown in Table 7. The PPG 1000-containing saccharification enzyme aqueous solution was employed as comparative sample 16. Notably, in Table 7, the component concentration of comparative sample 16 represents the corresponding concentration of the PPG 1000-containing saccharification enzyme aqueous solution.

(2-5. Saccharification Enzyme Aqueous Solution Containing Silica)

A saccharification enzyme aqueous solution containing silica was produced through the following procedure.

To deionized water, 1M acetate buffer (for adjusting pH to 5.0), silica, and the cellulase aqueous solution prepared in 2-1. were added, so that the buffer concentration was adjusted to 0.05 M. The silica was an alkaline silica sol (pH: 9.3, silica concentration: 40 mass %) containing dense spherical colloidal silica (mean primary particle size: 85 nm) produced through the water glass method and dispersed in water. The mixture was stirred at room temperature by means of a rotor which was rotated at 100 rpm for 30 minutes, to thereby prepare a silica-containing saccharification enzyme aqueous solution having a saccharification enzyme concentration (cellulase concentration in the Example) and a silica concentration shown in Table 7. The silica-containing saccharification enzyme aqueous solution was employed as comparative sample 17. Notably, in Table 7, the component concentration of comparative sample 17 represents the corresponding concentration of the silica-containing saccharification enzyme aqueous solution.

TABLE 7

| | Cellulase | | Silica sol | | PPG 1000 | | |
| --- | --- | --- | --- | --- | --- | --- | --- |
| | Cellulase from | Cellulase concn. mass % | Mean primary particle size nm | Silica concn. mass % | PPG 1000 concn. mass % | PPG 1000/ silica wt. ratio | pH |
| sample 21 | Undisclosed | 0.06 | 85 | 0.2 | 0.05 | 0.25 | 5.0 |
| comp. sample 15 | Undisclosed | 0.06 | — | — | — | — | 5.0 |
| comp. sample 16 | Undisclosed | 0.06 | — | — | 0.05 | — | 5.0 |
| comp. sample 17 | Undisclosed | 0.06 | 85 | 0.2 | — | — | 5.0 |

(2-6. Saccharification Reaction Mixture)

To the saccharification enzyme composition of sample 21, microcrystalline cellulose powder was added. The powder was dispersed in the composition, to thereby prepare a saccharification reaction mixture. The specific procedure is as follows.

Firstly, each sample (10 mL) was placed in a glass bottle (capacity: 13.5 mL). While the contents were stirred by means of a stirrer (4 mmϕ×10 mm length), microcrystalline cellulose powder (crystal type: I, Avicel PH-101, product of Sigma Aldrich) was added in an amount of 1.00 g (equivalent to 100 mg/mL). Then, the bottle was tightly closed with a stopper.

Also, the procedure of preparing the saccharification enzyme composition of sample 21 was repeated, except that saccharification enzyme aqueous solution (comparative sample 15), PPG 1000-containing saccharification enzyme aqueous solution (comparative sample 16), and silica-containing saccharification enzyme aqueous solution (comparative sample 17) were used, to thereby yield the corresponding saccharification reaction mixtures of comparative samples.

(2-7. Production of Saccharide)

A saccharification reaction mixture employing each of the aforementioned samples and comparative samples was caused to be reacted enzymatically in a thermostatic bath (50° C.) under stirring for 3 days, to thereby form a saccharide (glucose).

(2-8. Calculation of Glucose Formation Amount)

Example 21

In a manner similar to that employed in Example 1, the saccharification reaction mixture obtained from the saccharification enzyme composition of sample 21 (hereinafter, the reaction mixture will be referred to as "saccharification reaction mixture of Example 21") was subjected to enzymatic reaction (2-7.). Three days after the enzymatic reaction, the amount of formed glucose was calculated. Table 8 shows the results.

Comparative Examples 15 to 17

In a manner similar to that employed in Example 1, each of the saccharification reaction mixtures obtained from the saccharification enzyme aqueous solution of comparative sample 15, the PPG 1000-containing saccharification enzyme aqueous solution of comparative sample 16, and the silica-containing saccharification enzyme aqueous solution of comparative sample 17 (hereinafter, the reaction mixtures will be referred to as "saccharification reaction mixture of Comparative Examples 15 to 17", respectively) was subjected to enzymatic reaction (2-7.). Three days after the enzymatic reaction, the amount of formed glucose was calculated. Table 8 shows the results.

adding silica to the cellulase aqueous solution; and the saccharification reaction mixture of Example 21, prepared by adding silica and PPG 1000 to the cellulase aqueous solution, an increase in glucose formation amount was observed in the case of the saccharification reaction mixture of Example 21, prepared by adding silica and PPG 1000 to the cellulase aqueous solution, confirming enhancement in saccharification reaction efficiency. Therefore, even when a commercial cellulase was used, enhancement in saccharification reaction efficiency was confirmed through combination use of silica and PPG 1000.

[3. Production of Saccharide by Use of Diatomaceous Earth as "Silica or Silica-Containing Substance"]

(3-1. Mean Secondary Particle Size)

The mean secondary particle size of diatomaceous earth particles was measured by means of the following analyzer:
Laser diffraction particle size analyzer: LA-300 (product of HORIBA Ltd.)

(3-2. Cellulase Aqueous Solution)

A cellulase aqueous solution was produced through the following procedure.

A powder of a cellulase mixture having a specific component ratio was added to deionized water, and the mixture was stirred at room temperature by means of a rotor which was rotated at 100 rpm for 30 minutes, to thereby prepare a cellulase aqueous solution. The cellulase mixture serving as a saccharification enzyme was a mixture (7:3 (w/w)) of a cellulase originating from the *Trichoderma reesei* (*T. reesei*) (product of Sigma Aldrich) and a cellulase originating from the *Aspergillus niger* (*A. niger*) (product of MP Biomedicals). The cellulase mixture exhibits an optimum enzymatic activity within a pH range of 3 to 6.

TABLE 8

| | | | Enzym. reaction conditions | | | |
|---|---|---|---|---|---|---|
| | Saccharification enzyme aq. soln. | | Cellulose concn. mg/mL | Reaction temp. ° C. | Reaction time day | Glucose amount mg/mL |
| Ex. 21 | Saccharification enzyme compn. | sample 21 | 100 | 50 | 3 | 66.5 |
| Comp. 15 | Saccharification enzyme aq. soln. | comp. sample 15 | 100 | 50 | 3 | 61.3 |
| Comp. 15 | PPG-1000-containing saccharification enzyme aq. soln. | comp. sample 16 | 100 | 50 | 3 | 62.0 |
| Comp. 17 | Silica-containing saccharification enzyme aq. soln. | comp. sample 17 | 100 | 50 | 3 | 63.8 |

(2-8. Saccharification Reaction Efficiency)

Saccharification reaction efficiency of each saccharification reaction mixture was assessed on the basis of the glucose formation amount shown in Table 8. Firstly, from the glucose formation amounts obtained in Examples 21, and Comparative Examples 15 to 17, the effect of PPG 1000 addition on enhancement in saccharification reaction efficiency was investigated.

FIG. 4 is a graph showing enhancement in saccharification reaction efficiency through addition of PPG 1000 (Example 21 and Comparative Examples 15 to 17). As shown in FIG. 4, among the saccharification reaction mixture of Comparative Example 15; the saccharification reaction mixture of Comparative Example 16, prepared by adding PPG 1000 to the cellulase aqueous solution; the saccharification reaction mixture of Comparative Example 17, prepared by (3-3. Saccharification Enzyme Composition)

A saccharification enzyme composition was produced through the following procedure.

To deionized water, 1M acetate buffer (for adjusting pH to 5.0), a silica-containing substance, compound (A), and the cellulase aqueous solution prepared in 3-2. were added, so that the buffer concentration was adjusted to 0.05 M. The silica-containing substance used was diatomaceous earth (Oplite P-1200, product of Chuo Silika Co., Ltd., silica content: 90 mass %, mean secondary particle size: 15 μm), and PPG 1000 was used as compound (A) similar to 2-2. The mixture was stirred at room temperature by means of a rotor which was rotated at 100 rpm for 30 minutes, to thereby prepare a saccharification enzyme composition having a saccharification enzyme concentration (cellulase concentration in the Examples), a diatomaceous earth concentration, and a PPG 1000 concentration, shown in Table 9. The saccharification enzyme composition was employed as sample 22. Notably, in Table 9, the component concentration of sample 22 represents the corresponding concentration of the saccharification enzyme composition.

The procedure of preparing sample 22 was repeated, except that diatomaceous earth products having different mean secondary particle sizes were used, to thereby prepare saccharification enzyme compositions. These saccharification enzyme compositions were employed as samples 23 to 28 shown in Table 9. Notably, in Table 9, the component concentration of each of samples 23 to 28 represents the corresponding concentration of the saccharification enzyme composition.

TABLE 9

| | Cellulase | | Diatomaceous earth | | PPG 1000 | | |
| | Cellulase from | Cellulase concn. mass % | Type | Mean secondary particle size μm | Diatomaceous earth concn. (silica concn.) mass % | PPG 1000 concn. mass % | PPG 1000/ silica wt. ratio | pH |
|---|---|---|---|---|---|---|---|---|
| sample 22 | T. reesei A. niger | 0.02 | N | 15 | 1 (0.9) | 0.1 | 0.11 | 5.0 |
| sample 23 | T. reesei A. niger | 0.02 | O | 19 | 1 (0.9) | 0.1 | 0.11 | 5.0 |
| sample 24 | T. reesei A. niger | 0.02 | P | 19 | 1 (0.9) | 0.1 | 0.11 | 5.0 |
| sample 25 | T. reesei A. niger | 0.02 | Q | 30 | 0.11 (0.1) | 0.1 | 1 | 5.0 |
| sample 26 | T. reesei A. niger | 0.02 | Q | 30 | 1 (0.9) | 0.1 | 0.11 | 5.0 |
| sample 27 | T. reesei A. niger | 0.02 | R | 38 | 1 (0.9) | 0.1 | 0.11 | 5.0 |
| sample 28 | T. reesei A. niger | 0.02 | S | 25 | 1 (0.9) | 0.1 | 0.11 | 5.0 |

The symbols N to S of diatomaceous earth products shown in Table 9 are as follows:
N: Oplite P-1200, product of Chuo Silika Co., Ltd., silica content: 90 mass %, mean secondary particle size: 15 μm
O: Silica #100F, product of Chuo Silika Co., Ltd., silica content: 90 mass %, mean secondary particle size: 19 μm
P: Silica #300S, product of Chuo Silika Co., Ltd., silica content: 90 mass %, mean secondary particle size: 19 μm
Q: Silica #600S, product of Chuo Silika Co., Ltd., silica content: 90 mass %, mean secondary particle size: 30 μm
R: Silica #600H, product of Chuo Silika Co., Ltd., silica content: 90 mass %, mean secondary particle size: 38 μm
S: Silica Queen L, product of Chuo Silika Co., Ltd., silica content: 90 mass %, mean secondary particle size: 25 μm (3-4. Saccharification Enzyme Aqueous Solution)

A saccharification enzyme composition was produced through the following procedure.

To deionized water, 1M acetate buffer (for adjusting pH to 5.0) and the cellulase aqueous solution prepared in 3-2. were added, so that the buffer concentration was adjusted to 0.05 M. The mixture was stirred at room temperature by means of a rotor which was rotated at 100 rpm for 30 minutes, to thereby prepare a saccharification enzyme aqueous solution having a saccharification enzyme concentration (cellulase concentration in the Example) shown in Table 10. The saccharification enzyme aqueous solution was employed as comparative sample 18.

(3-5. Saccharification Enzyme Aqueous Solution Containing PPG 1000)

A saccharification enzyme composition containing PPG 1000 as compound (A) was produced through the following procedure.

To deionized water, 1M acetate buffer (for adjusting pH to 5.0), PPG 1000, and the cellulase aqueous solution prepared in 3-2. were added, so that the buffer concentration was adjusted to 0.05 M. The mixture was stirred at room temperature by means of a rotor which was rotated at 100 rpm for 30 minutes, to thereby prepare a PPG 1000-containing saccharification enzyme aqueous solution having a saccharification enzyme concentration (cellulase concentration in the Example) and a PPG 1000 concentration, shown in Table 10. The PPG 1000-containing saccharification enzyme aqueous solution was employed as comparative sample 19. Notably, in Table 10, the component concentration of comparative sample 19 represents the corresponding concentration of the PPG 1000-containing saccharification enzyme aqueous solution.

(3-6. Saccharification Enzyme Aqueous Solution Containing Diatomaceous Earth)

A saccharification enzyme composition containing diatomaceous earth was produced through the following procedure.

To deionized water, 1M acetate buffer (for adjusting pH to 5.0), a silica-containing substance, and the cellulase aqueous solution prepared in 3-2. were added, so that the buffer concentration was adjusted to 0.05 M. The silica-containing substance used was diatomaceous earth (Oplite P-1200, product of Chuo Silika Co., Ltd., silica content: 90 mass %, mean secondary particle size: 15 μm). The mixture was stirred at room temperature by means of a rotor which was rotated at 100 rpm for 30 minutes, to thereby prepare a diatomaceous earth-containing saccharification enzyme aqueous solution having a saccharification enzyme concentration (cellulase concentration in the Example) and a diatomaceous earth concentration, shown in Table 10. The diatomaceous earth-containing saccharification enzyme aqueous solution was employed as comparative sample 20. Notably, in Table 10, the component concentration of comparative sample 20 represents the corresponding concentration of the diatomaceous earth-containing saccharification enzyme aqueous solution.

The procedure of preparing comparative sample 20 was repeated, except that diatomaceous earth products having different mean secondary particle sizes were used, to thereby prepare diatomaceous earth-containing saccharification enzyme aqueous solutions. These saccharification enzyme compositions were employed as comparative samples 21 to 26 shown in Table 10. Notably, in Table 10, the component concentration of each of comparative samples 21 to 26 represents the corresponding concentration of the diatomaceous earth-containing saccharification enzyme aqueous solution.

TABLE 10

| | Cellulase | | Diatomaceous earth | | PPG 1000 | | |
| | | | Mean secondary | Diatomaceous | | | |
| | Cellulase from | Cellulase concn. mass % | Type | particle size μm | earth concn. (silica concn.) mass % | PPG 1000 concn. mass % | PPG 1000/ silica wt. ratio | pH |
|---|---|---|---|---|---|---|---|---|
| comp. sample 18 | T. reesei A. niger | 0.02 | — | — | — | — | — | 5.0 |
| comp. sample 19 | T. reesei A. niger | 0.02 | — | — | — | 0.1 | — | 5.0 |
| comp. sample 20 | T. reesei A. niger | 0.02 | N | 15 | 1 (0.9) | — | — | 5.0 |
| comp. sample 21 | T. reesei A. niger | 0.02 | O | 19 | 1 (0.9) | — | — | 5.0 |
| comp. sample 22 | T. reesei A. niger | 0.02 | P | 19 | 1 (0.9) | — | — | 5.0 |
| comp. sample 23 | T. reesei A. niger | 0.02 | Q | 30 | 0.11 (0.1) | — | — | 5.0 |
| comp. sample 24 | T. reesei A. niger | 0.02 | Q | 30 | 1 (0.9) | — | — | 5.0 |
| comp. sample 25 | T. reesei A. niger | 0.02 | R | 38 | 1 (0.9) | — | — | 5.0 |
| comp. sample 26 | T. reesei A. niger | 0.02 | S | 25 | 1 (0.9) | — | — | 5.0 |

The symbols N to S of diatomaceous earth products shown in Table 10 are as follows:
N: Oplite P-1200, product of Chuo Silika Co., Ltd., silica content: 90 mass %, mean secondary particle size: 15 μm
O: Silica #100F, product of Chuo Silika Co., Ltd., silica content: 90 mass %, mean secondary particle size: 19 μm
P: Silica #300S, product of Chuo Silika Co., Ltd., silica content: 90 mass %, mean secondary particle size: 19 μm
Q: Silica #600S, product of Chuo Silika Co., Ltd., silica content: 90 mass %, mean secondary particle size: 30 μm
R: Silica #600H, product of Chuo Silika Co., Ltd., silica content: 90 mass %, mean secondary particle size: 38 μm
S: Silica Queen L, product of Chuo Silika Co., Ltd., silica content: 90 mass %, mean secondary particle size: 25 μm (3-7. Saccharification Reaction Mixture)

To each of the saccharification enzyme compositions of samples 22 to 28, microcrystalline cellulose powder was added. The powder was dispersed in the composition, to thereby prepare a saccharification reaction mixture employing the corresponding sample. The specific procedure is as follows.

Firstly, each sample (10 mL) was placed in a glass bottle (capacity: 13.5 mL). While the contents were stirred by means of a stirrer (4 mmφ×10 mm length), microcrystalline cellulose powder (crystal type: I, Avicel PH-101, product of Sigma Aldrich) was added in an amount of 0.50 g (equivalent to 50 mg/mL). Then, the bottle was tightly closed with a stopper.

Also, the procedure of preparing the saccharification enzyme compositions of samples 21 to 28 was repeated, except that saccharification enzyme aqueous solution (comparative sample 18), PPG 1000-containing saccharification enzyme aqueous solution (comparative sample 19), and diatomaceous earth-containing saccharification enzyme aqueous solutions (comparative samples 20 to 26) were used, to thereby yield the corresponding saccharification reaction mixtures of comparative samples.

(3-8. Production of Saccharide)

A saccharification reaction mixture employing each of the aforementioned samples and comparative samples was caused to be reacted enzymatically in a thermostatic bath (40° C.) under stirring for 3 days, to thereby form a saccharide (glucose).

(3-9. Calculation of Glucose Formation Amount)

Examples 22 to 28

In a manner similar to that employed in Example 1, the saccharification reaction mixtures obtained from the saccharification enzyme compositions of samples 22 to 28 (hereinafter, the reaction mixtures will be referred to as "saccharification reaction mixtures of Examples 22 to 28") were subjected to enzymatic reaction (3-8.). Three days after the enzymatic reaction, the amount of formed glucose was calculated. Table 11 shows the results.

TABLE 11

| | Saccharification enzyme compn. | Enzym. reaction conditions | | | Glucose amount mg/mL |
| | | Cellulose concn. mg/mL | Reaction temp. ° C. | Reaction time day | |
|---|---|---|---|---|---|
| Ex. 22 | sample 22 | 50 | 40 | 3 | 33.0 |
| Ex. 23 | sample 23 | 50 | 40 | 3 | 33.8 |
| Ex. 24 | sample 24 | 50 | 40 | 3 | 33.3 |
| Ex. 25 | sample 25 | 50 | 40 | 3 | 32.4 |
| Ex. 26 | sample 26 | 50 | 40 | 3 | 34.0 |
| Ex. 27 | sample 27 | 50 | 40 | 3 | 32.5 |
| Ex. 28 | sample 28 | 50 | 40 | 3 | 33.4 |

Comparative Examples 18 to 26

In the same manner as employed in Example 1, the saccharification reaction mixture obtained from the saccharification enzyme aqueous solution (comparative sample 18), PPG 1000-containing saccharification enzyme aqueous solution (comparative sample 19), and diatomaceous earth-containing saccharification enzyme aqueous solution (comparative samples 20 to 26) (hereinafter, the reaction mixtures will be referred to as "saccharification reaction mixtures of Comparative Examples 18 to 26") were subjected to enzymatic reaction (3-8.). Three days after the enzymatic reaction, the amount of formed glucose from each mixture was calculated. Table 12 shows the results.

TABLE 12

| Comp. Exs. | Saccharification enzyme aq. solns. | | Enzym. reaction conditions | | | |
|---|---|---|---|---|---|---|
| | | | Cellulose concn. mg/mL | Reaction temp. ° C. | Reaction time day | Glucose amount mg/mL |
| 18 | Saccharification enzyme aq. soln. | comp. sample 18 | 50 | 40 | 3 | 29.6 |
| 19 | PPG 1000-containing saccharification enzyme aq. soln. | comp. sample 19 | 50 | 40 | 3 | 28.9 |
| 20 | Diat. earth-containing saccharification enzyme aq. soln. | comp. sample 20 | 50 | 40 | 3 | 29.7 |
| 21 | Diat. earth-containing saccharification enzyme aq. soln. | comp. sample 21 | 50 | 40 | 3 | 31.2 |
| 22 | Diat. earth-containing saccharification enzyme aq. soln. | comp. sample 22 | 50 | 40 | 3 | 30.2 |
| 23 | Diat. earth-containing saccharification enzyme aq. soln. | comp. sample 23 | 50 | 40 | 3 | 29.6 |
| 24 | Diat. earth-containing saccharification enzyme aq. soln. | comp. sample 24 | 50 | 40 | 3 | 32.0 |
| 25 | Diat. earth-containing saccharification enzyme aq. soln. | comp. sample 25 | 50 | 40 | 3 | 31.7 |
| 26 | Diat. earth-containing saccharification enzyme aq. soln. | comp. sample 26 | 50 | 40 | 3 | 31.2 |

(3-10. Saccharification Reaction Efficiency)

Saccharification reaction efficiency of each saccharification reaction mixture was assessed on the basis of the glucose formation amount shown in Table 11 or 12. Firstly, from the glucose formation amounts obtained in Examples 22 to 28, and Comparative Examples 18 to 26, the effect of PPG 1000 addition on enhancement in saccharification reaction efficiency was investigated.

FIG. 5 is a graph showing enhancement in saccharification reaction efficiency through addition of PPG 1000 (Examples 22 to 28, and Comparative Examples 18 to 26). As shown in FIG. 5, among the saccharification reaction mixture of Comparative Example 18; the saccharification reaction mixture of Comparative Example 19, prepared by adding PPG 1000 to the cellulase aqueous solution; the saccharification reaction mixtures of Comparative Examples 20 to 26, prepared by adding diatomaceous earth to the cellulase aqueous solution; and the saccharification reaction mixtures of Examples 22 to 28, prepared by adding diatomaceous earth and PPG 1000 to the cellulase aqueous solution, an increase in glucose formation amount was observed in the saccharification reaction mixtures of Examples 22 to 28, prepared by adding diatomaceous earth and PPG 1000 to the cellulase aqueous solution, confirming enhancement in saccharification reaction efficiency. Therefore, when diatomaceous earth was used as a silica-containing substance in combination with PPG 1000 in saccharification reaction, enhancement in saccharification reaction efficiency was confirmed.

[4. Production of Saccharide by Use of Silica Sand as "Silica or Silica-Containing Substance"]

(4-1. Mean Primary Particle Size)

The mean primary particle size of silica sand was measured by means of the following analyzer. In the measurement, 100 particles were observed (×50), and longer diameter measurements were arithmetically averaged.

Metallurgical microscope: ECLIPSE ME 600D (product of Nikon Instech. Co., Ltd.)

(4-2. Cellulase Aqueous Solution)

A cellulase aqueous solution was produced through the following procedure.

A powder of a cellulase mixture having a specific component ratio was added to deionized water, and the mixture was stirred at room temperature by means of a rotor which was rotated at 100 rpm for 30 minutes, to thereby prepare a cellulase aqueous solution. The cellulase mixture serving as a saccharification enzyme was a mixture (7:3 (w/w)) of a cellulase originating from the *Trichoderma reesei* (*T. reesei*) (product of Sigma Aldrich) and a cellulase originating from the *Aspergillus niger* (*A. niger*) (product of MP Biomedicals). The cellulase mixture exhibits an optimum enzymatic activity within a pH range of 3 to 6.

(4-3. Saccharification Enzyme Composition)

A saccharification enzyme composition was produced through the following procedure.

To deionized water, 1M acetate buffer (for adjusting pH to 5.0), a silica-containing substance, compound (A), and the cellulase aqueous solution prepared in 4-2. were added, so that the buffer concentration was adjusted to 0.05 M. The silica-containing substance was silica sand (No. 5, product of Toyo Matelan Co., Ltd., silica content: 95 mass %, mean primary particle size: 310 μm), and PPG 1000 was used as compound (A) similar to 2-2. The mixture was stirred at room temperature by means of a rotor which was rotated at 100 rpm for 30 minutes, to thereby prepare a saccharification enzyme composition having a saccharification enzyme concentration (cellulase concentration in the Examples), a silica sand concentration, and a PPG 1000 concentration, shown in Table 13. The saccharification enzyme composition was employed as sample 29. Notably, in Table 13, the component concentration of sample 29 represents the corresponding concentration of the saccharification enzyme composition.

The procedure of preparing sample 29 was repeated, except that 2,4,7,9-tetramethyl-5-decyne-4,7-diol ethylene oxide adduct (ethylene oxide addition (mol); m+n=10) was used as compound (A), to thereby prepare a saccharification enzyme composition. The saccharification enzyme composition was employed as sample 30 shown in Table 13. Notably, in Table 13, the component concentration of sample 30 represents the corresponding concentration of the saccharification enzyme composition.

(4-4. Saccharification Enzyme Aqueous Solution Containing Compound (A))

A saccharification enzyme aqueous solution containing PPG 1000 as compound (A) was prepared through the following procedure.

To deionized water, 1M acetate buffer (for adjusting pH to 5.0), PPG 1000, and the cellulase aqueous solution prepared in 4-2. were added, so that the buffer concentration was adjusted to 0.05 M. The mixture was stirred at room temperature by means of a rotor which was rotated at 100 rpm for 30 minutes, to thereby prepare a compound (A)-containing saccharification enzyme aqueous solution having a saccharification enzyme concentration (cellulase concentration in the Example) and a PPG 1000 concentration, shown in Table 13. The compound (A)-containing saccharification enzyme aqueous solution was employed as comparative sample 27. Notably, in Table 13, the component concentration of comparative sample 27 represents the corresponding concentration of the compound (A)-containing saccharification enzyme aqueous solution.

The procedure of preparing comparative sample 27 was repeated, except that 2,4,7,9-tetramethyl-5-decyne-4,7-diol ethylene oxide adduct (ethylene oxide addition (mol); m+n=10) was used as compound (A), to thereby prepare a compound (A)-containing saccharification enzyme aqueous solution. The compound (A)-containing saccharification enzyme aqueous solution was employed as comparative sample 28 shown in Table 13. Notably, in Table 13, the component concentration of comparative sample 28 represents the corresponding concentration of the compound (A)-containing saccharification enzyme aqueous solution.

(4-5. Saccharification Enzyme Aqueous Solution Containing Silica Sand)

A saccharification enzyme aqueous solution containing silica sand was produced through the following procedure.

To deionized water, 1M acetate buffer (for adjusting pH to 5.0), a silica-containing substance, and the cellulase aqueous solution prepared in 4-2. were added, so that the buffer concentration was adjusted to 0.05 M. The silica-containing substance was silica sand (No. 5, product of Toyo Matelan Co., Ltd., silica content: 95 mass %, mean primary particle size: 310 μm). The mixture was stirred at room temperature by means of a rotor which was rotated at 100 rpm for 30 minutes, to thereby prepare a silica sand-containing saccharification enzyme aqueous solution having a saccharification enzyme concentration (cellulase concentration in the Example) and a silica sand concentration, shown in Table 13. The silica sand-containing saccharification enzyme aqueous solution was employed as comparative sample 29. Notably, in Table 13, the component concentration of comparative sample 29 represents the corresponding concentration of the silica sand-containing saccharification enzyme aqueous solution.

TABLE 13

| | Cellulase | | Silica sand | | compd. (A) | | |
|---|---|---|---|---|---|---|---|
| | Cellulase from | Cellulase concn. mass % | Mean primary particle size μm | Silica sand concn. (silica concn.) mass % | Type | compd. (A) concn. mass % | compd. (A)/ silica wt. ratio | pH |
| sample 29 | T. reesei A. niger | 0.003 | 310 | 1 (0.95) | U | 0.1 | 0.1 | 5.0 |
| sample 30 | T. reesei A. niger | 0.003 | 310 | 1 (0.95) | V | 0.1 | 0.1 | 5.0 |
| comp. sample 1 | T. reesei A. niger | 0.003 | — | — | — | — | — | 5.0 |
| comp. sample 27 | T. reesei A. niger | 0.003 | — | — | U | 0.1 | — | 5.0 |
| comp. sample 28 | T. reesei A. niger | 0.003 | — | — | V | 0.1 | — | 5.0 |
| comp. sample 29 | T. reesei A. niger | 0.003 | 310 | 1 (0.95) | — | — | — | 5.0 |

In Table 13, symbols U and V of compound (A) are as follows:
U: polypropylene glycol (average molecular weight: 1,000)
V: 2,4,7,9-tetramethyl-5-decyne-4,7-diol ethylene oxide adduct (ethylene oxide addition (mol); m + n = 10) (Surfynol 465, product of Nissin Chemical Industry Co., Ltd.)

(4-6. Saccharification Reaction Mixture)

The procedure of producing saccharification enzyme compositions of samples 1 to 18 was repeated, except that the saccharification enzyme compositions of samples 29 and 30, compound (A)-containing saccharification enzyme aqueous solutions of comparative samples 27 and 28, and silica-containing saccharification enzyme aqueous solution of comparative sample 29 were used, to thereby prepare saccharification reaction mixtures of samples 29 and 30, and comparative samples 27 to 29.

(4-7. Production of Saccharide)

In a manner similar to Example 1, saccharification reaction mixtures employing each of the aforementioned samples and comparative samples were caused to be reacted enzymatically in a thermostatic bath (25° C.) under stirring for two days, to thereby form a saccharide (glucose).

(4-8. Calculation of Glucose Formation Amount)

Examples 29 and 30

In a manner similar to that employed in Example 1, the saccharification reaction mixtures obtained from the saccharification enzyme compositions of samples 29 and 30 (hereinafter, the reaction mixtures will be referred to as "saccharification reaction mixtures of Examples 29 and 30") were subjected to enzymatic reaction (4-7.). Two days after the enzymatic reaction, the amount of formed glucose was calculated. Table 14 shows the results.

Comparative Examples 27 to 29

In the same manner as employed in Example 1, saccharification reaction mixtures obtained from the saccharification enzyme aqueous solutions containing compound (A) of comparative sample 27 or 28, and from the silica sand-containing saccharification enzyme aqueous solution of comparative sample 29 (hereinafter, the reaction mixtures will be referred to as "saccharification reaction mixtures of Comparative Examples 27 to 29") were subjected to enzymatic reaction (4-7.). Two days after the enzymatic reaction, the amount of formed glucose from each mixture was calculated. Table 14 shows the results.

reaction solution of Comparative Example 1; the saccharification reaction mixtures of Comparative Examples 27 and 28, prepared by adding PPG 1000 and 2,4,7,9-tetramethyl-5-decyne-4,7-diol ethylene oxide adduct to the cellulase aqueous solution; and the saccharification reaction mixture of Comparative Example 29, prepared by adding silica sand to the cellulase aqueous solution; and the saccharification reaction mixtures of Examples 29 and 30, prepared by adding silica sand and PPG 1000, or silica sand and 2,4,7,9-tetramethyl-5-decyne-4,7-diol ethylene oxide adduct to the cellulase aqueous solution, an increase in glucose formation amount was observed in the saccharification reaction mixtures of Examples 29 and 30, prepared by adding silica sand and PPG 1000, or silica sand and 2,4,7,9-tetramethyl-5-decyne-4,7-diol ethylene oxide adduct to the cellulase aqueous solution, confirming enhancement in saccharification reaction efficiency. Therefore, when silica sand (i.e., as silica-containing substance) was used in combination with PPG 1000 or 2,4,7,9-tetramethyl-5-decyne-4,7-diol ethylene oxide adduct in cellulose saccharification reaction, enhancement in saccharification reaction efficiency was confirmed.

[5. Production of Ethanol by Use of Saccharide]

(5-1. Yeast Aqueous Solution)

A yeast aqueous solution was prepared through the following procedure.

To deionized water (40 g) preliminarily maintained at 35° C., yeast powder (0.2 g) was added, and the mixture was maintained at 35° C. While the mixture was maintained at

TABLE 14

| | | | Enzym. reaction conditions | | | |
|---|---|---|---|---|---|---|
| | Saccharification enzyme aq. solns. | | Cellulose concn. mg/mL | Reaction temp. ° C. | Reaction time day | Glucose amount mg/mL |
| Ex. 29 | Saccharification enzyme compn. | sample 29 | 5 | 25 | 2 | 3.48 |
| Ex. 30 | Saccharification enzyme compn. | sample 30 | 5 | 25 | 2 | 3.46 |
| Comp. 1 | Saccharification enzyme aq. soln. | comp. sample 1 | 5 | 25 | 2 | 2.91 |
| Comp. 27 | Compd. (A)-containing saccharification enzyme aq. soln. | comp. sample 27 | 5 | 25 | 2 | 3.10 |
| Comp. 28 | Compd. (A)-containing saccharification enzyme aq. soln. | comp. sample 28 | 5 | 25 | 2 | 3.05 |
| Comp. 29 | Silica sand-containing saccharification enzyme aq. soln. | comp. sample 29 | 5 | 25 | 2 | 3.27 |

(4-9. Saccharification Reaction Efficiency)

Saccharification reaction efficiency of each saccharification reaction mixture was assessed on the basis of the glucose formation amount shown in Table 14. Firstly, from the glucose formation amounts obtained in Examples 29 and 30, and Comparative Examples 1, and 27 to 29, the effect of addition of PPG 1000 or 2,4,7,9-tetramethyl-5-decyne-4,7-diol ethylene oxide adduct on enhancement in saccharification reaction efficiency was investigated.

FIG. 6 is a graph showing enhancement in saccharification reaction efficiency through addition of PPG 1000 or 2,4,7,9-tetramethyl-5-decyne-4,7-diol ethylene oxide adduct (Examples 29 and 30, and Comparative Examples 1, and 27 to 29). As shown in FIG. 6, among the saccharification 35° C., the contents were dissolved by stirring the mixture by means of a magnetic stirrer for 20 minutes, to thereby yield a 0.5-mass % (i.e., yeast powder (0.2 g)/deionized water (40 g)) yeast aqueous solution. As the yeast, *Saccharomyces cerevisiae* (*S. cerevisiae*) YP2 (product of Sigma Aldrich) belonging to the *Saccharomyces* was used.

(5-2. Ethanol Fermentation Aqueous Solution)

An ethanol fermentation aqueous solution was prepared through the following procedure.

To deionized water, sulfuric acid, urea, the cellulase aqueous solution prepared in 1-2, and the yeast aqueous solution prepared in 5-1. were added, so that the final pH and the nitrogen source concentration were adjusted to about 5 and 0.21 mg/mL, respectively. The mixture was stirred at room temperature by means of a magnetic stirrer for 10 minutes, to thereby prepare an ethanol fermentation aqueous solution having a saccharification enzyme concentration (cellulase concentration in the Examples) and a yeast concentration shown in Table 15. The ethanol fermentation aqueous solution was employed as comparative sample 30.
(5-3. Ethanol Fermentation Composition)

An ethanol enzyme composition was prepared through the following procedure.

To deionized water, sulfuric acid, urea, the cellulase aqueous solution prepared in 1-2, a silica-containing substance, compound (A), and the yeast aqueous solution prepared in 5-1. were added, so that the final pH and the nitrogen source concentration were adjusted to about 5 and 0.21 mg/mL, respectively. The silica-containing substance was an alkaline silica sol (pH: 9.5, silica concentration: 40 mass %) containing dense spherical colloidal silica (mean primary particle size: 85 nm) produced through the water glass method and dispersed in water, and compound (A) was PPG 1000 as employed in 2-2. The mixture was stirred at room temperature by means of a magnetic stirrer for 10 minutes, to thereby prepare an ethanol fermentation composition having a saccharification enzyme concentration (cellulase concentration in the Examples), a silica concentration, a PPG 1000 concentration, and a yeast concentration shown in Table 15. The ethanol fermentation composition was employed as sample 31. Notably, in Table 15, the component concentration of sample 31 represents the corresponding concentration of the ethanol fermentation composition.
(5-4. Ethanol Fermentation Aqueous Solution Containing PPG 1000)

A PPG 1000-containing ethanol fermentation aqueous solution was prepared through the following procedure.

To deionized water, sulfuric acid, urea, PPG 1000 (as compound (A)), the cellulase aqueous solution prepared in 1-2, and the yeast aqueous solution prepared in 5-1. were added, so that the final pH and the nitrogen source concentration were adjusted to about 5 and 0.21 mg/mL, respectively. The mixture was stirred at room temperature by means of a magnetic stirrer for 10 minutes, to thereby prepare a PPG 1000-containing ethanol fermentation aqueous solution having a saccharification enzyme concentration, a PPG 1000 concentration, and a yeast concentration, shown in Table 15. The PPG 1000-containing ethanol fermentation aqueous solution was employed as comparative sample 31. Notably, in Table 15, the component concentration of comparative sample 31 represents the corresponding concentration of the PPG 1000-containing ethanol fermentation aqueous solution.
(5-5. Ethanol Fermentation Aqueous Solution Containing Silica)

A silica-containing ethanol fermentation aqueous solution was prepared through the following procedure.

To deionized water, sulfuric acid, urea, silica, the cellulase aqueous solution prepared in 1-2, and the yeast aqueous solution prepared in 5-1. were added, so that the final pH and the nitrogen source concentration were adjusted to about 5 and 0.21 mg/mL, respectively. The silica was an alkaline silica sol (pH: 9.5, silica concentration: 40 mass %) containing dense spherical colloidal silica (mean primary particle size: 85 nm) produced through the water glass method and dispersed in water. The mixture was stirred at room temperature by means of a rotor which was rotated at 100 rpm for 30 minutes, to thereby prepare a silica-containing ethanol fermentation aqueous solution having a saccharification enzyme concentration (cellulase concentration in the Examples), a silica concentration, and a yeast concentration, shown in Table 15. The silica-containing ethanol fermentation aqueous solution was employed as comparative sample 32. Notably, in Table 15, the component concentration of comparative sample 32 represents the corresponding concentration of the silica-containing ethanol fermentation aqueous solution.

TABLE 15

| | | Cellulase | | Silica sol | | PPG 1000 | | Aq. yeast soln. | | |
| | | | | Mean primary | | | | | | |
| | Cellulase from | Saccharification enzyme concn. mass % | particle size nm | Silica concn. mass % | PPG 1000 concn. mass % | PPG 1000/ silica wt. ratio | Yeast from | Yeast concn. mass % | pH |
|---|---|---|---|---|---|---|---|---|---|---|
| sample 31 | T. reesei A. niger | 0.01 | 85 | 0.5 | 0.05 | 0.1 | S. cerevisiae | 0.05 | 5.3 |
| comp. sample 30 | T. reesei A. niger | 0.01 | — | — | — | — | S. cerevisiae | 0.05 | 4.9 |
| comp. sample 31 | T. reesei A. niger | 0.01 | — | — | 0.05 | — | S. cerevisiae | 0.05 | 5.0 |
| comp. sample 32 | T. reesei A. niger | 0.01 | 85 | 0.5 | — | — | S. cerevisiae | 0.05 | 5.3 |

(5-6. Saccharification Reaction/Ethanol Fermentation Mixture)

To the ethanol fermentation composition of sample 31, microcrystalline cellulose powder was added. The powder was dispersed in the composition, to thereby prepare a saccharification reaction/ethanol fermentation mixture employing sample 31. The specific procedure is as follows.

Firstly, sample 31 (10 mL) was placed in a glass bottle (capacity: 13.5 mL). While the contents were stirred by means of a stirrer (4 mmϕ×10 mm length), microcrystalline cellulose powder (crystal type: I, Avicel PH-101, product of Sigma Aldrich) was added in an amount of 0.20 g (equivalent to 20 mg/mL). Then, the bottle was closed with a silicone stopper equipped with a hydrophobic PTEF membrane filter (absolute pore size: 0.22 μm).

Also, the procedure of preparing the ethanol fermentation composition of sample 31 was repeated, except that ethanol fermentation aqueous solution (comparative sample 30), PPG 1000-containing ethanol fermentation aqueous solution (comparative sample 31), and silica-containing substance-containing ethanol fermentation aqueous solution (comparative sample 32) were used, to thereby yield the corresponding saccharification reaction/ethanol fermentation mixtures of comparative samples.
(5-7. Production of Ethanol)

A saccharification reaction/ethanol fermentation mixture employing each of the aforementioned samples and comparative samples was caused to be reacted enzymatically in a thermostatic bath (31° C.) under stirring for two days. During reaction, a saccharide (glucose) was formed, and ethanol fermentation was simultaneously performed by use of the formed saccharide, to thereby produce ethanol.
(5-8. Calculation of Ethanol Formation Amount)

Example 31

The saccharification reaction/ethanol fermentation mixture obtained from the ethanol fermentation composition of sample 31 (hereinafter, the reaction mixture will be referred to as "saccharification reaction/ethanol fermentation mixture of Example 31") was subjected to enzymatic reaction and ethanol fermentation. After the enzymatic reaction and ethanol fermentation, the amount of formed ethanol was calculated through gas chromatography (GC).

The saccharification reaction/ethanol fermentation mixture of Example 31 (0.5 mL) was sampled into a microtube (2 mL), and the enzyme and yeast in the tube was deactivated at 105° C. for 15 minutes. Then, the reaction mixture was centrifuged by means of a high speed refrigerated centrifuge SRX-201 (product of Tomy Seiko Co., Ltd.) at 15,000 G for 30 minutes, so as to remove unreacted cellulose, the silica-containing substance, and yeast. Thereafter, the supernatant was recovered. Ethanol formation amount was determined by means of a gas chromatograph GC-2014s (product of Shimadzu Corporation) through the one-point calibration method. Table 16 shows the ethanol formation amount measurements (mg/mL).

The specific analytical conditions are as follows.
<Analytical Conditions>
Column: Polar Pack Q, length: 1 m, I.D.: 3.2 mm (product of GL Science)
Detector: FID
Column temperature: 150° C.
Flow rate: 40 mL/min
Sample amount: 2 μL
Standard: 10 mg/mL Ethanol aqueous solution Comparative Examples 30 to 32

In the same manner as that of Example 31, each of the saccharification reaction/ethanol fermentation mixtures obtained from ethanol fermentation aqueous solution (comparative sample 30), PPG 1000-containing ethanol fermentation aqueous solution (comparative sample 31), and silica-containing substance-containing ethanol fermentation aqueous solution (comparative sample 32) (hereinafter, the mixtures will be referred to as "saccharification reaction/ethanol fermentation mixtures of Comparative Examples 30 to 32") were subjected to saccharification reaction and ethanol fermentation of 5-7. Two days thereafter, the amount of formed ethanol was calculated. Table 16 shows the results.

TABLE 16

| | Saccharification reaction/EtOH fermentation mixtures | | Enzym. reaction conditions | | | |
|---|---|---|---|---|---|---|
| | | | Cellulose concn. mg/mL | Reaction temp. ° C. | Reaction time day | EtOH amount mg/mL |
| Ex. 31 | EtOH fermentation compn. | sample 31 | 20 | 31 | 2 | 3.64 |
| Comp. 30 | EtOH fermentation aq. soln. | comp. sample 30 | 20 | 31 | 2 | 2.32 |
| Comp. 31 | PPG 1000-containing EtOH fermentation aq. soln. | comp. sample 31 | 20 | 31 | 2 | 2.28 |
| Comp. 32 | Silica-containing substance-containing EtOH fermentation aq. soln. | comp. sample 32 | 20 | 31 | 2 | 3.31 |

(5-9. Ethanol Fermentation Efficiency)

Ethanol fermentation efficiency of each saccharification reaction/ethanol fermentation mixture was assessed on the basis of the ethanol formation amount shown in Table 16. From the ethanol formation amounts obtained in Example 31 and Comparative Examples 30 to 32, the effect of PPG 1000 addition on enhancement in saccharification reaction efficiency was investigated.

FIG. 7 is a graph showing enhancement in ethanol fermentation efficiency through addition of PPG 1000 (Example 31 and Comparative Examples 30 to 32). As shown in FIG. 7, in comparison of saccharification reaction/ethanol fermentation mixture of Comparative Example 30 with that of Comparative Example 32, the mixture of Comparative Example 32, prepared by adding silica to the cellulase aqueous solution and the yeast aqueous solution, exhibited an increase in ethanol formation amount, indicating enhancement in ethanol formation efficiency. Also, in comparison of saccharification reaction/ethanol fermentation mixture of Example 31 with that of Comparative Example 32, the mixture of Example 31, prepared by adding silica and PPG 1000 to the cellulase aqueous solution and the yeast aqueous solution, exhibited an increase in ethanol formation amount, indicating further enhancement in ethanol formation efficiency. In contrast, in comparison of saccharification reaction/ethanol fermentation mixture of Comparative Example 30 with that of Comparative Example 31, even when PPG 1000 was added to the corresponding cellulase aqueous solution and yeast aqueous solution, no effect of enhancing ethanol formation efficiency was observed. Therefore, in cellulose saccharification reaction and ethanol fermentation, enhancement in ethanol formation efficiency was confirmed through combination use of a silica-containing substance and PPG 1000.

INDUSTRIAL APPLICABILITY

The present invention can be applied to an industrial field where saccharification technique is employed to form a saccharide such as glucose from a cellulosic biomass (including cellulose and hemicellulose). One such application is production of bioethanol from a cellulose material.

The invention claimed is:

1. A saccharification reaction mixture, wherein the reaction mixture can saccharify at least one member selected from the group consisting of cellulose and hemicellulose and comprises
    at least one member selected from the group consisting of cellulose and hemicellulose,
    a saccharification enzyme,
    silica, wherein the silica is colloidal silica having a mean primary particle size of 1 nm to 400 nm, and
    at least one compound (A) selected from the group consisting of propylene glycol, dipropylene glycol, tripropylene glycol, 1,3-butanediol, glycerol, pentaerythritol, polypropylene glycol, and propylene glycol 1-monomethyl ether; and
    wherein a ratio by mass of compound (A) to silica (compound (A)/silica) is 0.0001 to 1.

2. A saccharification enzyme composition, wherein the composition can saccharify at least one member selected from the group consisting of cellulose and hemicellulose and comprises
    a saccharification enzyme,
    silica, wherein the silica is colloidal silica having a mean primary particle size of 1 nm to 400 nm, and
    at least one compound (A) selected from the group consisting of propylene glycol, dipropylene glycol, tripropylene glycol, 1,3-butanediol, glycerol, pentaerythritol, polypropylene glycol, and propylene glycol 1-monomethyl ether; and
    wherein a ratio by mass of compound (A) to silica (compound (A)/silica) is 0.0001 to 1.

3. A method for producing a saccharide by use of a saccharification reaction mixture which can saccharify at least one member selected from the group consisting of cellulose and hemicellulose, wherein the method comprises employing a saccharification reaction mixture comprising
    at least one member selected from the group consisting of cellulose and hemicellulose,
    a saccharification enzyme, silica, wherein the silica is colloidal silica having a mean primary particle size of 1 nm to 400 nm, and
    at least one compound (A) selected from the group consisting of propylene glycol, dipropylene glycol, tripropylene glycol, 1,3-butanediol, glycerol, pentaerythritol, polypropylene glycol, and propylene glycol 1-monomethyl ether; and
    wherein a ratio by mass of compound (A) to silica (compound (A)/silica) is 0.0001 to 1.

4. A method for producing ethanol, wherein the method comprises subjecting a saccharide produced through a production method as recited in claim 3 to ethanol fermentation in the presence of a fermentation microorganism, to thereby produce ethanol.

5. An ethanol production method according to claim 4, wherein the fermentation microorganism is added to the saccharide production method, to thereby simultaneously carry out sugar production and ethanol fermentation.

6. An ethanol production method according to claim 4, wherein the fermentation microorganism is a yeast, a mold, or a bacterium.

7. An ethanol production method according to claim 6, wherein the fermentation microorganism is a microorganism belonging to the *Saccharomyces,* a microorganism belonging to the *Zymomonas,* a microorganism belonging to the *Pichia,* a microorganism belonging to the *Candida,* a microorganism belonging to the *Zymobacter,* a microorganism belonging to the *Corynebacterium,* a microorganism belonging to the *Kluyveromyces,* or a microorganism belonging to the *Escherichia.*

8. An ethanol production method according to claim 4 wherein ethanol fermentation is carried out at 15° C. to 35° C.

* * * * *